US011162949B2

(12) United States Patent
Mizumura et al.

(10) Patent No.: US 11,162,949 B2
(45) Date of Patent: Nov. 2, 2021

(54) METHOD FOR PRODUCING FACTOR C RECOMBINANT PROTEIN AND ENDOTOXIN-MEASURING AGENT

(71) Applicant: SEIKAGAKU CORPORATION, Tokyo (JP)

(72) Inventors: Hikaru Mizumura, Tokyo (JP); Maki Aizawa, Tokyo (JP); Toshio Oda, Tokyo (JP)

(73) Assignee: Seikagaku Corporation, Tokyo (JP)

( * ) Notice: Subject to any disclaimer, the term of this patent is extended or adjusted under 35 U.S.C. 154(b) by 79 days.

(21) Appl. No.: 15/984,288

(22) Filed: May 18, 2018

(65) Prior Publication Data

US 2018/0259527 A1 Sep. 13, 2018

Related U.S. Application Data

(63) Continuation of application No. 15/359,058, filed on Nov. 22, 2016, now abandoned, which is a continuation of application No. 14/704,230, filed on May 5, 2015, now abandoned, which is a continuation of application No. 14/001,138, filed as application No. PCT/JP2012/055728 on Feb. 28, 2012, now abandoned.

(60) Provisional application No. 61/447,556, filed on Feb. 28, 2011.

(51) Int. Cl.
*C12Q 1/34* (2006.01)
*C12Q 1/37* (2006.01)
*G01N 33/579* (2006.01)

(52) U.S. Cl.
CPC .......... *G01N 33/579* (2013.01); *C12Q 1/34* (2013.01); *C12Q 1/37* (2013.01); *G01N 2333/195* (2013.01); *G01N 2333/43508* (2013.01); *G01N 2333/96411* (2013.01); *G01N 2400/50* (2013.01)

(58) Field of Classification Search
CPC ... C12N 9/64; C12Q 1/37; G01N 2333/96411
USPC .................................................. 435/226, 15
See application file for complete search history.

(56) References Cited

U.S. PATENT DOCUMENTS

| 5,550,030 | A  | * | 8/1996 | Tanaka ............ | G01N 33/579 435/23 |
| 6,849,426 | B2 | * | 2/2005 | Chen .............. | G01N 33/579 435/69.1 |
| 2009/0208995 | A1 | | 8/2009 | Tamura et al. | |

FOREIGN PATENT DOCUMENTS

| EP | 0291856 A2 | 11/1988 |
| EP | 2050820 A1 | 4/2009 |
| JP | 2011-244760 A1 | 12/2011 |
| WO | WO 99/15676 A2 | 4/1999 |
| WO | WO 03/002976 A2 | 1/2003 |
| WO | WO 2008/004674 A1 | 10/2008 |

OTHER PUBLICATIONS

Nakamura et al, Purification and Properties of Intracellular Clotting Factor, Factor B, from Horseshoe Crab (*Tachypleus tridentatus*) Hemocytes. J Biochem. Mar. 1986;99(3):847-57.*
Invitrogen_ pIZV5vector_kit, 2008, 44pages.*
Third-Party Observation filed in corresponding Japanese Patent Application No. 2018-074569 dated Jul. 23, 2019.
Morais, V.A., Expression and Characterization of Recombinant human α-3/4-fucosyltransferase III From Spodoptera frugiperda (Sf9) and Trichoplusia ni (Tn) Cells Using the Baculovirus Expression System, Biochem J. 353:719-725, 2001.
GenBank: S77063.1. Amino Acid Sequence of CrFC21 (factor C from Carcinoscorpius rotandicauuda), 1995.
Muta, T., et al., Horseshoe Crab Coagulation Factor B: A Unique Serine protease Zymogen Activated by Cleavage of an Ile-Ile Bond, The Journal of Biological Chemistry 268(28):21384-21388, 1993.
Wu, W.-T., et al., Biopharmaceutical Technology, 2013, partial translation only.
Opposition to a Patent filed towards the corresponding Japanese patent No. 6640267 on Aug. 4, 2020.
Hom and Volkman, BioTechniques, vol. 25, 1998, pp. 18-20.
L. Ikonomou, et al., Appl Microbiol Biotechnol, vol. 62, 2003, pp. 1-20.
Vassilis Douris, et al., Advances in Virus Research, vol. 68, 2006, pp. 113-156.
Hideki Yamaji, SCEJ, 42nd Autumn Meeting, 2010, p. 673.
Yuko Kawaguchi, et al., Journal of the Japanese Medical Association, 2012, vol. 8, No. 1, pp. 26-30.
Kathy Hancok, et al., Journal of Immunological Methods, vol. 330, 2008, pp. 130-136.
Search Report and Written Opinion issued in corresponding International Patent Application No. PCT/JP2012/055728 dated May 11, 2012.
Office Action issued in corresponding Chinese Patent Application No. 201280010708.4 dated Sep. 19, 2014.
Office Action issued in corresponding Chinese Patent Application No. 201280010708.4 dated May 5, 2015.
Office Action issued in corresponding European Patent Application No. 12 710 808.2 dated Jun. 24, 2014.
Office Action issued in corresponding Japanese Patent Application No. 2013-538748 dated Jan. 5, 2016.
Third-party Observation issued in corresponding Japanese Patent Application No. 2013-538748 dated May 27, 2016.

(Continued)

*Primary Examiner* — Sheridan Swope
(74) *Attorney, Agent, or Firm* — Knobbe, Martens, Olson & Bear, LLP

(57) ABSTRACT

A method for rapidly and highly sensitively measuring endotoxin relies on an endotoxin-measuring agent, which includes a factor C derived from *Tachypleus tridentatus* that does not have His-tag sequence at the C-terminus, a factor B of a horseshoe crab, and a proclotting enzyme of a horseshoe crab. Each of these proteins can be a recombinant protein obtainable by being expressed using a stably expressing cell line of an insect cell as a host.

10 Claims, 9 Drawing Sheets

Specification includes a Sequence Listing.

(56) References Cited

OTHER PUBLICATIONS

Notification of Reasons for Refusal issued in corresponding Japanese Patent Application No. 2013-538748 dated Aug. 23, 2016.
Ding, et al., Expression of Full Length and Deletion Homologues of Carcinoscorpius rotundicauda Factor C in *Saccharomyces cerevisiae*: Immunoreactivity and Endotoxin Binding, Journal of Endotoxin Research 4(1):33-43, 1997.
Iwanaga, The Limulus Clotting Reaction, Current Opinion in Immunology 5:74-82, 1993.
Maeda, et al., Effects of His-tag on the Molecular Surf Ace Functionalities of Cystatin C, Proceedings of Symposium of the Japan Society for Bioscience, Biotechnology, and Agrochemistry, p. 278, 3B01a11, 2008.
Mason, et al., Differential Effect of a His Tag at the N- and C-Termini: Functional Studies with Recombinant Human Serum Transferrin, Biochemistry 41:9448-9454, 2002.
Muta et al., Limulus factor C. An Endotoxin-Sensitive Serine Protease Zymogen With a Mosaic Structure of Complement-Like, Epidermal Growth Factor-Like, and Lectin-Like Domains, The Journal of Biological Chemistry 266(10):6554-6561, 1991.
Nakamura, et al., Lipopolysaccharide-Sensitive Serine-Protease Zymogen (Factor C) Found in Limulus Hemocytes, European Journal of Biochemistry 154:511-521,1986.
Nakamura, et al., Purification and Properties of Intracellular Clotting Factor, Factor B, from Horseshoe Crab (*Tachypleus tridentatus*) Hemocytes, The Journal of Biochemistry 99(3):847-857, 1986.
Novagen Molecular Biology Catalog 2009/2010, Merck Ltd., Japan, 2009, Insect Cell Expression Vector Selection Guide, p. 134.
Pui, et al., Yeast Recombinant Factor C From Horseshoe Crab Binds Endotoxin and Causes Bacteriostasis, Journal of Endotoxin Research 4(6):391-400, 1997.
Wang, et al., Functional Expression of Full Length Limulus Factor C in Stably Transformed Sf9 cells, Biotechnology Letters 23:71-76, 2001.
Wang, et al., Closing and Expression of Tachypleus Tridentatus Factor C, Acta Biochimica et Biophysica Sinica 34(1):77-82, 2002.
Decision of Refusal received in Japanese Patent Application No. 2013-538748 dated Dec. 13, 2017.
Ramage, P., et al., Snags With Tags: Some Observations Made With (His)6-Tagged Proteins, Life Science ews (Japan Ed.) 4, 2002.
Notification of Reasons for Refusal for corresponding Japanese Patent Application No. 2013-538748 dated Mar. 14, 2017.
Alignment Figure of Amino Acid Sequences (created by GENETYX) of Tachypleus tridentatus Factor C and Carcinoscorpius rotundicauda Factor C, Nov. 14, 2016.
Maekawa, Mass Production of Proteins Using Baculovirus-Insect Cell Expression System, Protein Science Society of Japan, Archives e022, vol. 1, 2008.
Service Information of Comprehensive and Quantitative Profiling of Biological Samples-Derived Sugar Chain, Sugar Chain Analysis Using Mass Spectrometry by Medicinal Chemistry Pharmaceutical Co., Ltd., Nov. 10, 2016, URL: [https://www.funakoshi.co.jp/contents/8053].
Service Information of Contract Analysis Service by Sumitomo Bakelite Co., Ltd., Nov. 10, 2016, URL: [http://www.sumibe.co.jp/product/s-bio/glycan/contract/].
Service Information of Sugar Chain Analysis Service by Cosmo Bio Co., Ltd., Nov. 8, 2016, URL: [http://www.cosmobio.co.jp/product/detail/lud_20101019.asp?entry _id=658 6].
Vector Map of pFastBac™1, multi-cloning site, Invitrogen Life Technologies, publication date unknown.

* cited by examiner

[Fig.1]
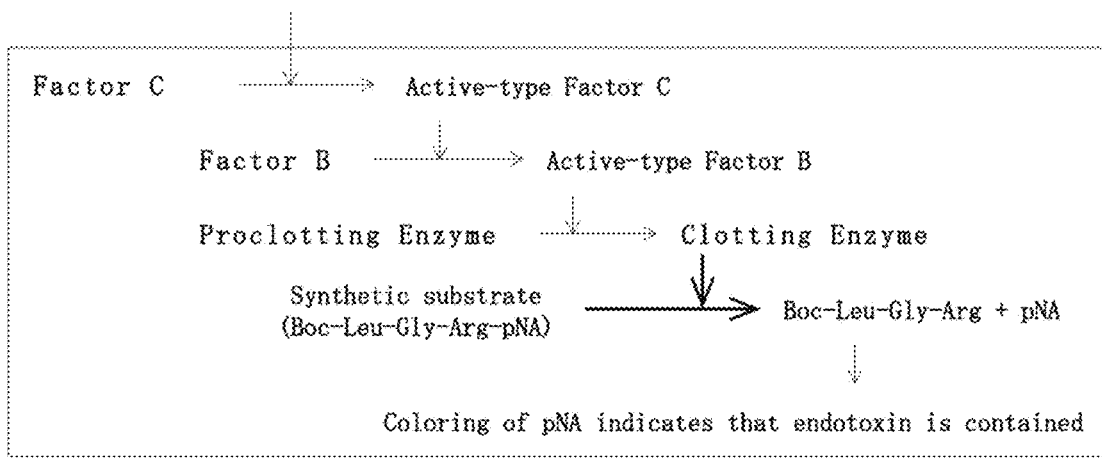

[Fig.2]
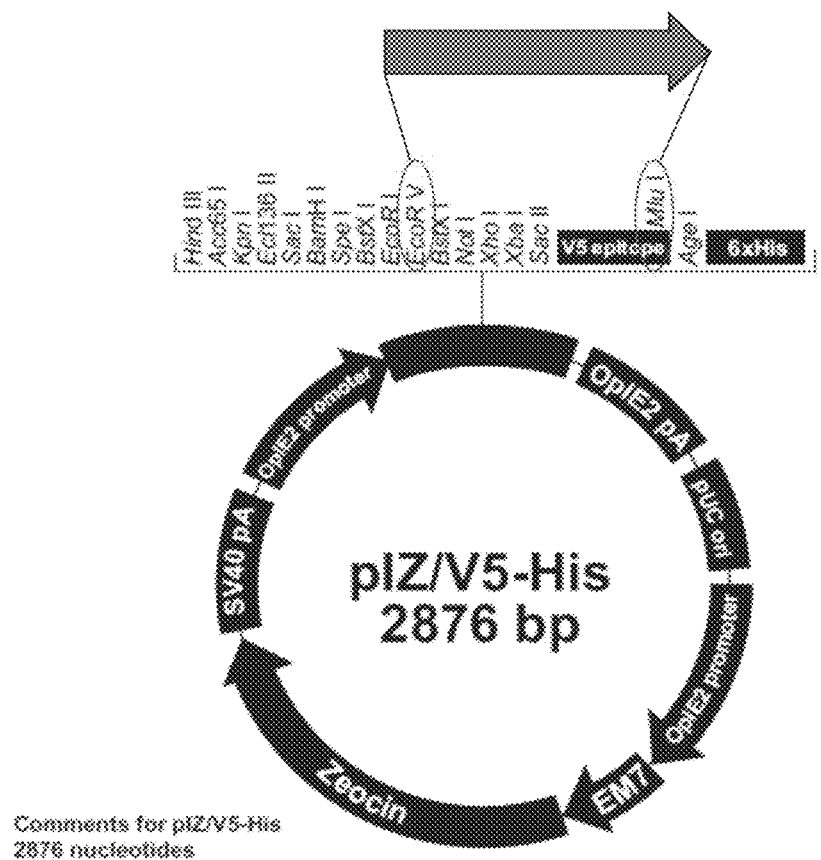

[Fig.3]
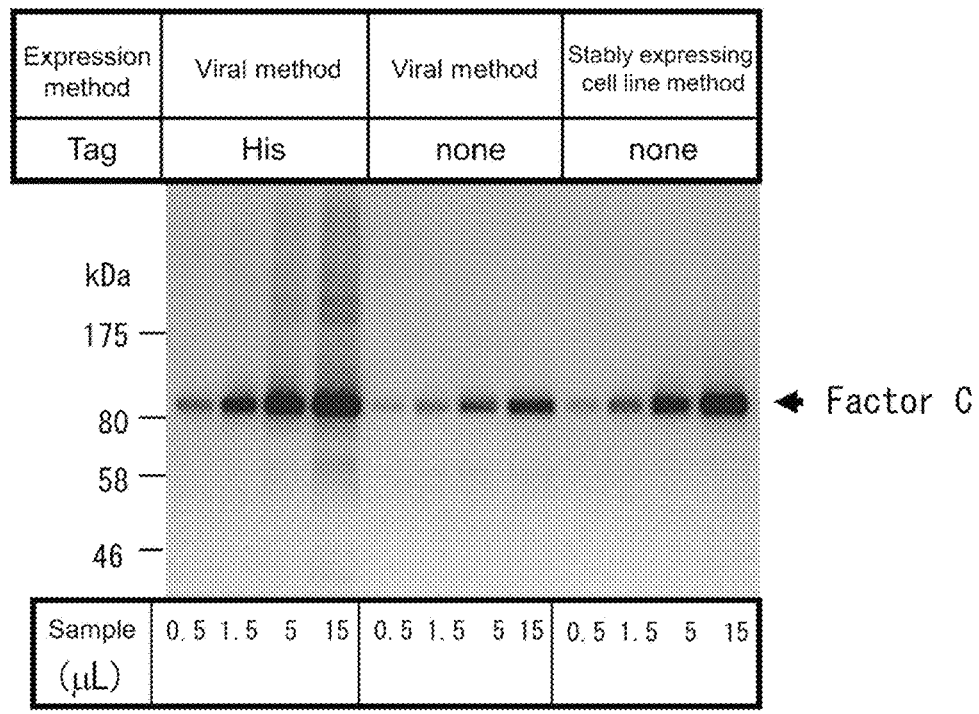
[Fig.4]
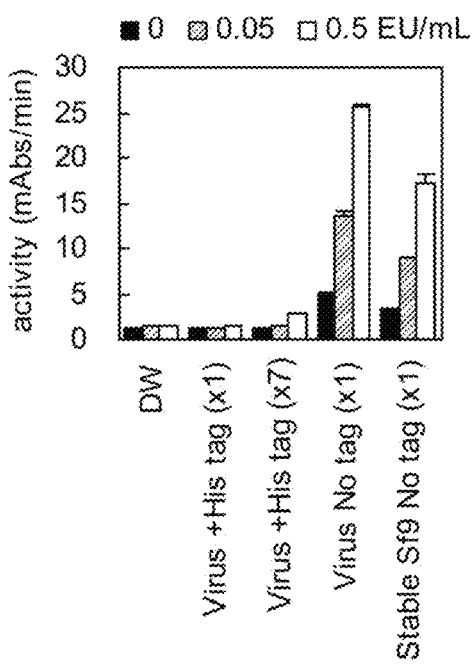

[Fig.5]
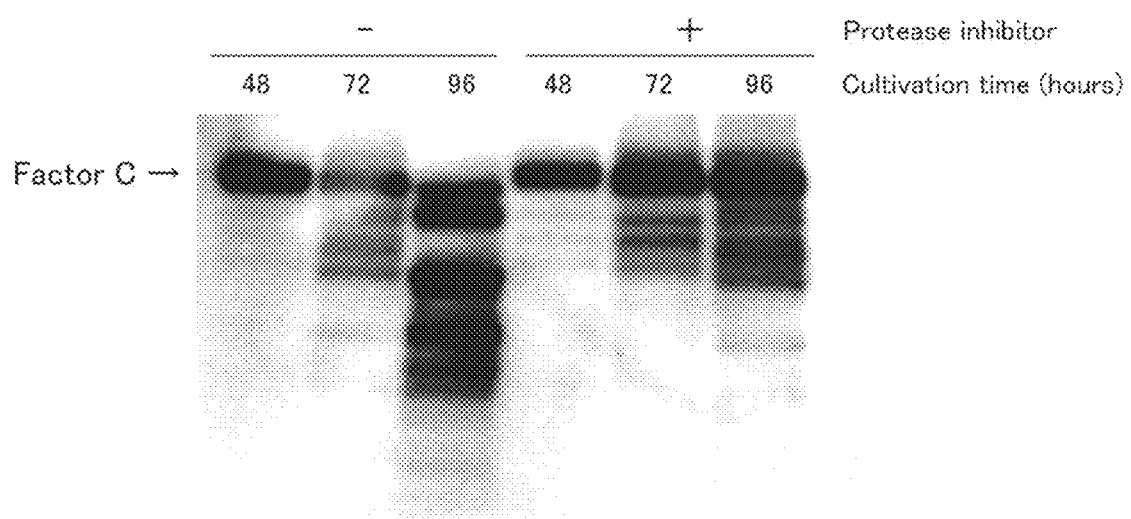

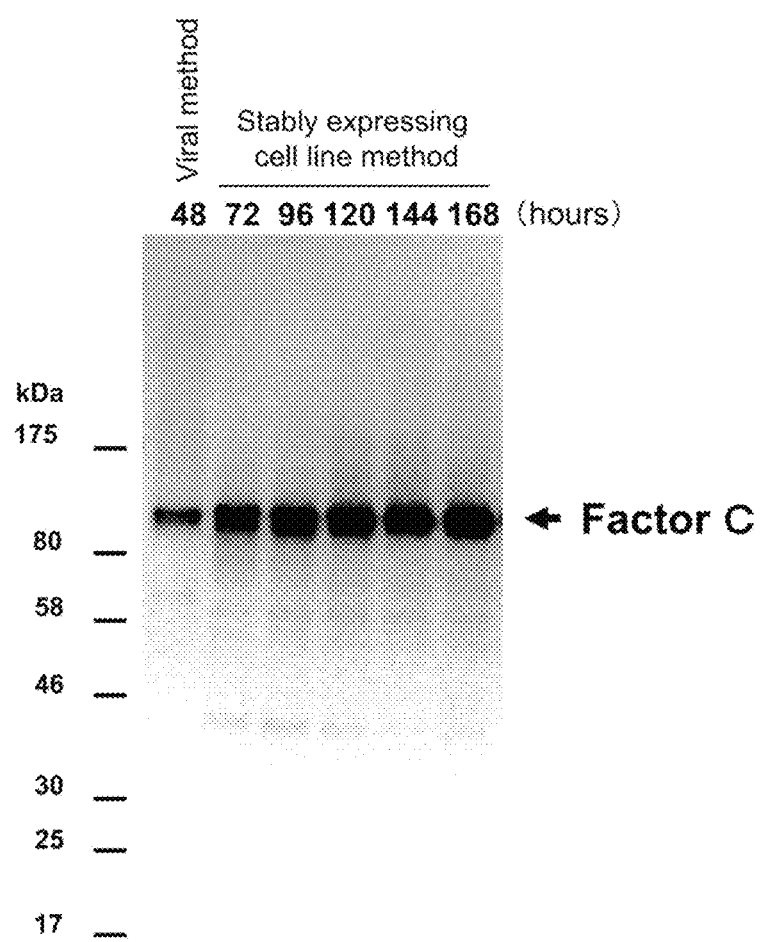
[Fig.6]

[Fig.7]
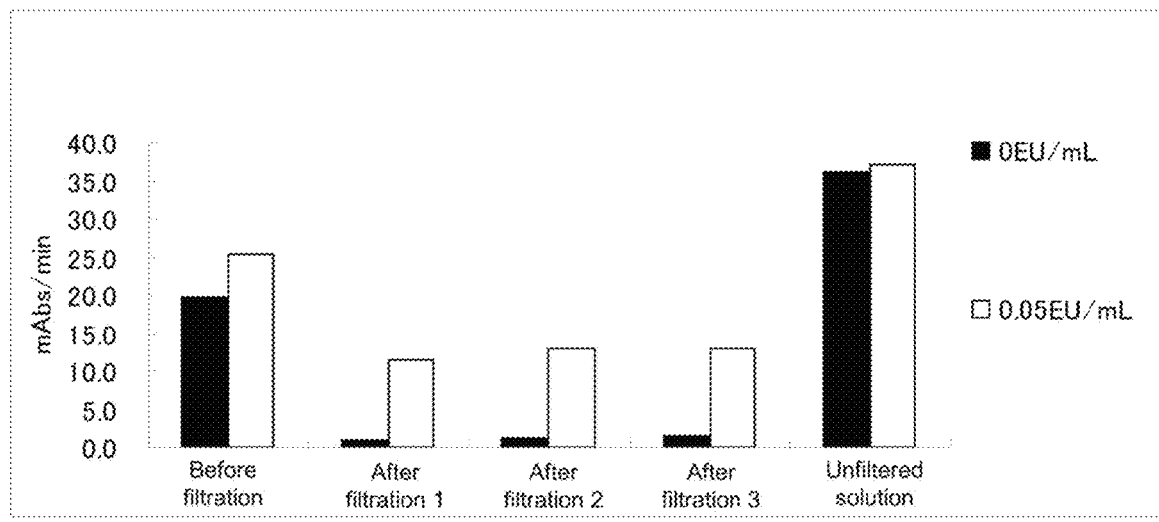
[Fig.8]
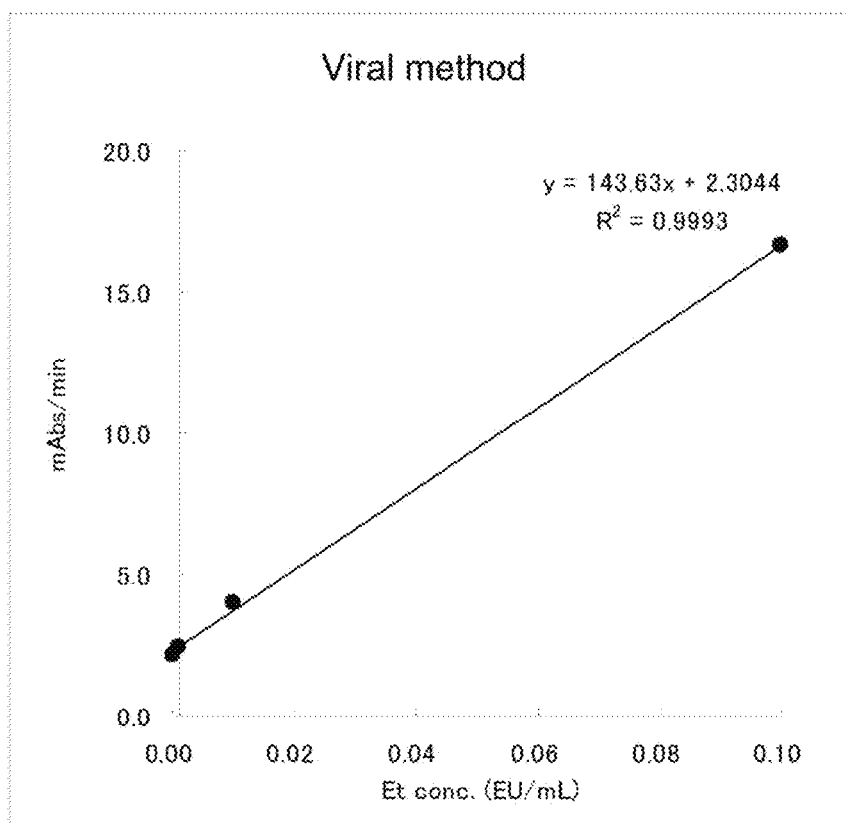

[Fig.9]
(a)
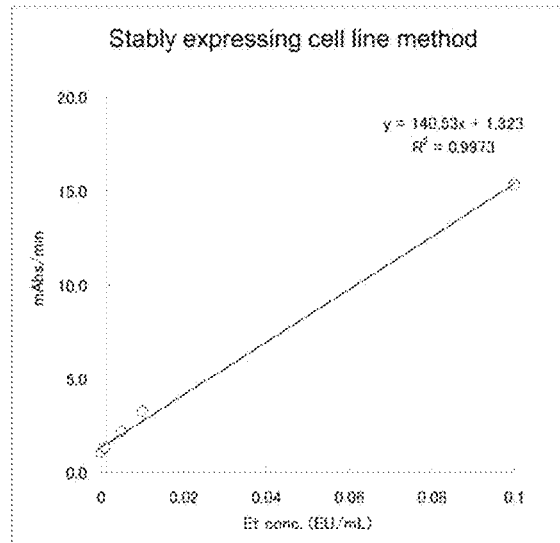
(b)
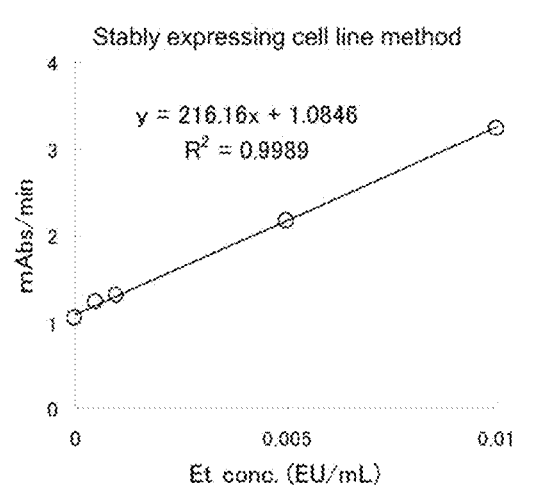

[Fig.10]
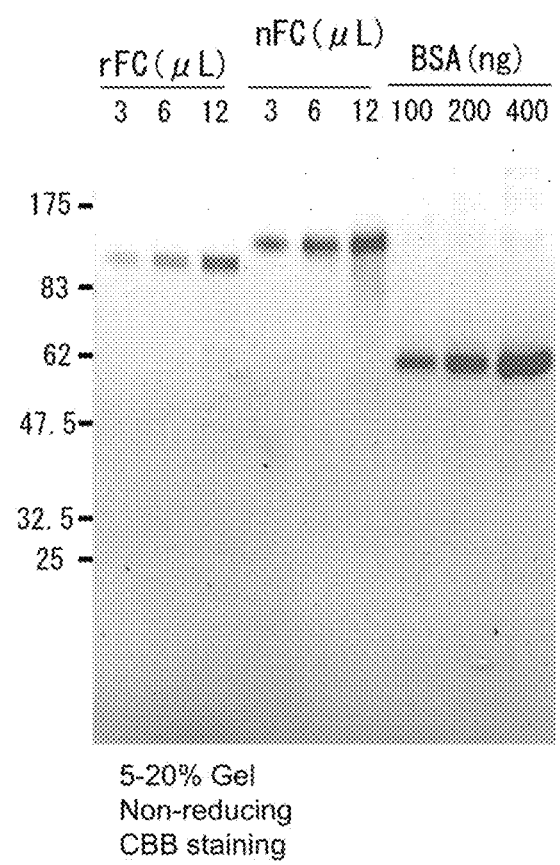

[Fig.11]
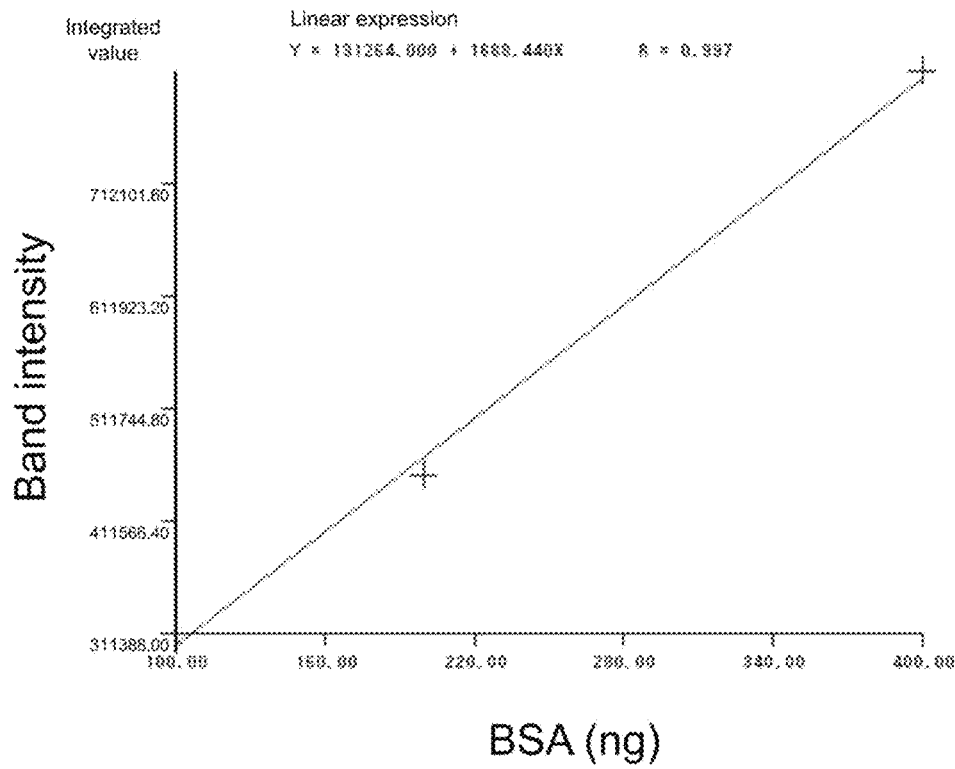
[Fig.12]
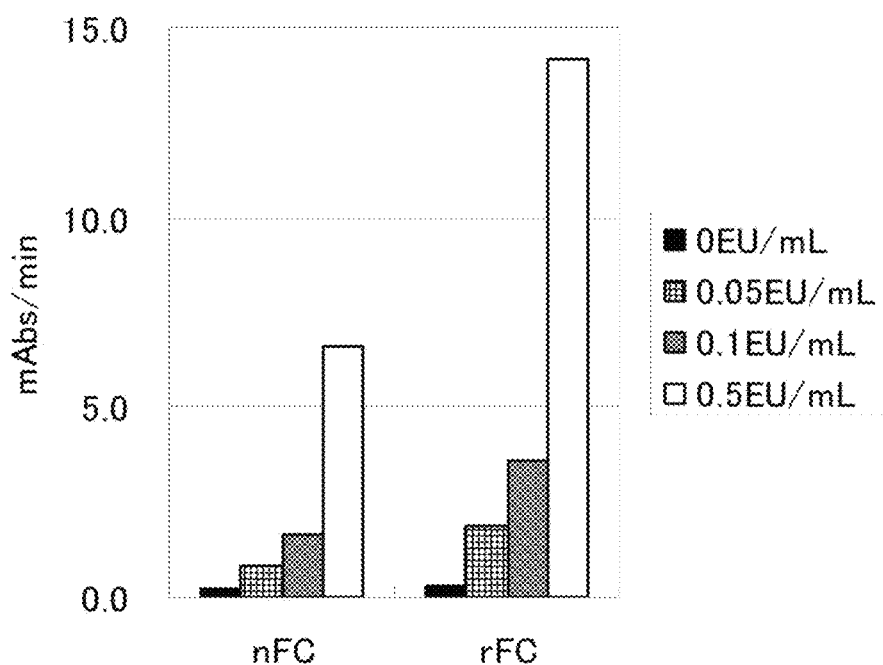

SEQUENCE LISTING

```
<160> NUMBER OF SEQ ID NOS: 12

<210> SEQ ID NO 1
<211> LENGTH: 3060
<212> TYPE: DNA
<213> ORGANISM: Tachypleus tridentatus
<220> FEATURE:
<221> NAME/KEY: CDS
<222> LOCATION: (1)..(3060)

<400> SEQUENCE: 1 atg gtc tta gcg tcg ttt ttg gtg tct ggt tta gtt cta ggg ata cta      48
Met Val Leu Ala Ser Phe Leu Val Ser Gly Leu Val Leu Gly Ile Leu
1               5                   10                  15 gcc caa caa atg cgt cca gtt cag tcc aga gga gta gat ctg ggc ttg      96
Ala Gln Gln Met Arg Pro Val Gln Ser Arg Gly Val Asp Leu Gly Leu
                20                  25                  30 tgt gat gaa acg agg ttc gag tgt aag tgt gga gat cca ggc tat gtg     144
Cys Asp Glu Thr Arg Phe Glu Cys Lys Cys Gly Asp Pro Gly Tyr Val
            35                  40                  45 ttc aac gtc cct atg aaa caa tgc acg tac tta tat cga tgg agg cct     192
```

```
                Phe Asn Val Pro Met Lys Gln Cys Thr Tyr Phe Tyr Arg Trp Arg Pro
                 50              55                  60 tat tgt aaa cca tgt gat gac ctg gag gct aag gac att tgt cca aag         240
Tyr Cys Lys Pro Cys Asp Asp Leu Glu Ala Lys Asp Ile Cys Pro Lys
 65              70                  75                  80 tac aaa cga tgt caa gag tgt aag gct ggt ctt gat agt tgt gtt act         288
Tyr Lys Arg Cys Gln Glu Cys Lys Ala Gly Leu Asp Ser Cys Val Thr
                 85                  90                  95 tgt cca cct aac aaa tat ggt act tgg tgt agc ggt gaa tgt caa tgt         336
Cys Pro Pro Asn Lys Tyr Gly Thr Trp Cys Ser Gly Glu Cys Gln Cys
             100                 105                 110 aag aat gga ggt atc tgt gac cag agg aca gga gct tgt acc tgt cgt         384
Lys Asn Gly Gly Ile Cys Asp Gln Arg Thr Gly Ala Cys Thr Cys Arg
             115                 120                 125 gac aga tat gaa gga gcg cac tgt gaa att ctc aaa ggt tgt cct ctt         432
Asp Arg Tyr Glu Gly Ala His Cys Glu Ile Leu Lys Gly Cys Pro Leu
             130                 135                 140 ctt cca tcg gat tct caa gtt cag gaa gtc aga aac cca cca gat aat         480
Leu Pro Ser Asp Ser Gln Val Gln Glu Val Arg Asn Pro Pro Asp Asn
145                 150                 155                 160 ccc caa act att gac tac agc tgt tca cca ggg ttc aag ctt aaa ggc         528
Pro Gln Thr Ile Asp Tyr Ser Cys Ser Pro Gly Phe Lys Leu Lys Gly
                 165                 170                 175 gtg gca cga att agc tgt ctc cca aat gga cag tgg agt agc ttt cca         576
Val Ala Arg Ile Ser Cys Leu Pro Asn Gly Gln Trp Ser Ser Phe Pro
             180                 185                 190 ccc aaa tgt att cga gaa tgt gcc aag gtt tca tct cca gaa cac ggg         624
Pro Lys Cys Ile Arg Glu Cys Ala Lys Val Ser Ser Pro Glu His Gly
             195                 200                 205 aaa gtg aat gct cct agt ggc aat atg ata gaa ggg gct act tta cgg         672
Lys Val Asn Ala Pro Ser Gly Asn Met Ile Glu Gly Ala Thr Leu Arg
             210                 215                 220 ttc tca tgt gat agt ccc tac tac ttg att ggt caa gaa aca tta acc         720
Phe Ser Cys Asp Ser Pro Tyr Tyr Leu Ile Gly Gln Glu Thr Leu Thr
225                 230                 235                 240 tgc cag ggt aat ggt cag tgg agt gga caa ata cca caa tgt aag aag         768
Cys Gln Gly Asn Gly Gln Trp Ser Gly Gln Ile Pro Gln Cys Lys Lys
                 245                 250                 255 ttg gtc ttc tgt cct gac ctt gat cct gta aac cat gct gaa cac cag         816
Leu Val Phe Cys Pro Asp Leu Asp Pro Val Asn His Ala Glu His Gln
             260                 265                 270 gtt aaa att ggt gtg gaa caa aaa tat ggt cag ttt cct caa ggc act         864
Val Lys Ile Gly Val Glu Gln Lys Tyr Gly Gln Phe Pro Gln Gly Thr
             275                 280                 285 gaa gtg acc tat acg tgt tcg ggt aac tac ttc ttg atg ggt ttt aac         912
Glu Val Thr Tyr Thr Cys Ser Gly Asn Tyr Phe Leu Met Gly Phe Asn
             290                 295                 300 acc tta aaa tgt aac cct gat ggg tcc tgg tca gga tca cag cca tcc         960
Thr Leu Lys Cys Asn Pro Asp Gly Ser Trp Ser Gly Ser Gln Pro Ser
305                 310                 315                 320 tgt gtt aaa gtg gca gac aga gag gtc gac tgt gac agt aaa gct gta        1008
Cys Val Lys Val Ala Asp Arg Glu Val Asp Cys Asp Ser Lys Ala Val
                 325                 330                 335 gac ttc ttg gat gat gtt ggt gaa cct gtc agg atc cac tgt cct gct        1056
Asp Phe Leu Asp Asp Val Gly Glu Pro Val Arg Ile His Cys Pro Ala
                 340                 345                 350 ggc tgt tct ttg aca gct ggt act gtg tgg ggt aca gcc ata tac cac        1104
Gly Cys Ser Leu Thr Ala Gly Thr Val Trp Gly Thr Ala Ile Tyr His
             355                 360                 365
```

```
gaa ctt tcc tca gtg tgt cgt gca gcc atc cat gct ggc aag ctt cca    1152
Glu Leu Ser Ser Val Cys Arg Ala Ala Ile His Ala Gly Lys Leu Pro
    370             375                 380 aac tct gga ggg gcg gtg cat gta gtg aac aat ggc ccc tac tcg gac    1200
Asn Ser Gly Gly Ala Val His Val Val Asn Asn Gly Pro Tyr Ser Asp
385             390                 395                 400 ttt ctg ggt agt gac ctg aat ggg ata aaa tcg gaa gag ttg aag tct    1248
Phe Leu Gly Ser Asp Leu Asn Gly Ile Lys Ser Glu Glu Leu Lys Ser
                405                 410                 415 ctt gcc cgc agt ttt cga ttt gat tat gtc agt tca tcc aca gca ggt    1296
Leu Ala Arg Ser Phe Arg Phe Asp Tyr Val Ser Ser Ser Thr Ala Gly
            420                 425                 430 aga tca gga tgt cct gat gga tgg ttt gag gta gaa gag aac tgt gtg    1344
Arg Ser Gly Cys Pro Asp Gly Trp Phe Glu Val Glu Glu Asn Cys Val
        435                 440                 445 tac gtt aca tca aaa cag aga gcc tgg gaa aga gct caa ggt gtg tgt    1392
Tyr Val Thr Ser Lys Gln Arg Ala Trp Glu Arg Ala Gln Gly Val Cys
    450                 455                 460 acc aat atg gct gct cgt ctt gct gtg cta gac aaa gat cta att ccg    1440
Thr Asn Met Ala Ala Arg Leu Ala Val Leu Asp Lys Asp Leu Ile Pro
465                 470                 475                 480 agt tcc ttg act gag act cta cga ggg aaa ggg tta aca acc aca tgg    1488
Ser Ser Leu Thr Glu Thr Leu Arg Gly Lys Gly Leu Thr Thr Thr Trp
                485                 490                 495 ata gga ttg cac aga cta gat gct gag aag ccc ttt gtt tgg gag cta    1536
Ile Gly Leu His Arg Leu Asp Ala Glu Lys Pro Phe Val Trp Glu Leu
            500                 505                 510 atg gat cgt agt aat gtg gtt ctg aat gat aac cta aca ttc tgg gcc    1584
Met Asp Arg Ser Asn Val Val Leu Asn Asp Asn Leu Thr Phe Trp Ala
        515                 520                 525 tct ggc gaa cct gga aat gaa act aac tgt gta tat ctg gac atc cga    1632
Ser Gly Glu Pro Gly Asn Glu Thr Asn Cys Val Tyr Leu Asp Ile Arg
    530                 535                 540 gat cag ctg cag cct gtg tgg aaa acc aag tca tgt ttt cag ccc tca    1680
Asp Gln Leu Gln Pro Val Trp Lys Thr Lys Ser Cys Phe Gln Pro Ser
545                 550                 555                 560 agc ttt gct tgc atg atg gat ttg tca gac aga aat aaa gcc aaa tgc    1728
Ser Phe Ala Cys Met Met Asp Leu Ser Asp Arg Asn Lys Ala Lys Cys
                565                 570                 575 gat gac cct gga cca ctg gaa aat gga cac gcc aca ctt cat gga caa    1776
Asp Asp Pro Gly Pro Leu Glu Asn Gly His Ala Thr Leu His Gly Gln
            580                 585                 590 agt att gat ggg ttc tat gct ggt tct tct ata agg tac agc tgt gag    1824
Ser Ile Asp Gly Phe Tyr Ala Gly Ser Ser Ile Arg Tyr Ser Cys Glu
        595                 600                 605 gtt ctc cac tac ctc agt gga act gag acc gta act tgt aca aca aat    1872
Val Leu His Tyr Leu Ser Gly Thr Glu Thr Val Thr Cys Thr Thr Asn
    610                 615                 620 ggc aca tgg agt gct cct aaa cct cga tgt atc aaa gtc atc acc tgc    1920
Gly Thr Trp Ser Ala Pro Lys Pro Arg Cys Ile Lys Val Ile Thr Cys
625                 630                 635                 640 caa aac cct cct gta cca tca tat ggt tct gtg gaa atc aaa ccc cca    1968
Gln Asn Pro Pro Val Pro Ser Tyr Gly Ser Val Glu Ile Lys Pro Pro
                645                 650                 655 agt cgg aca aac tcg atc agt cgt gtt ggg tca cct ttc ttg agg ttg    2016
Ser Arg Thr Asn Ser Ile Ser Arg Val Gly Ser Pro Phe Leu Arg Leu
            660                 665                 670 cca cgg tta ccc ctc cca tta gcc aga gca gcc aaa cct cct cca aaa    2064
Pro Arg Leu Pro Leu Pro Leu Ala Arg Ala Ala Lys Pro Pro Pro Lys
        675                 680                 685
```

-continued

| | | |
|---|---|---|
| cct aga tcc tca caa ccc tct act gtg gac ttg gct tct aaa gtt aaa<br>Pro Arg Ser Ser Gln Pro Ser Thr Val Asp Leu Ala Ser Lys Val Lys<br>690                       695                   700 | 2112 |
| cta cct gaa ggt cat tac cgg gta ggg tct cga gcc att tac acg tgc<br>Leu Pro Glu Gly His Tyr Arg Val Gly Ser Arg Ala Ile Tyr Thr Cys<br>705                     710                  715               720 | 2160 |
| gag tcg aga tac tac gaa cta ctt gga tct caa ggc aga aga tgt gac<br>Glu Ser Arg Tyr Tyr Glu Leu Leu Gly Ser Gln Gly Arg Arg Cys Asp<br>                   725                  730               735 | 2208 |
| tct aat gga aac tgg agt ggt cgg ccc gct agc tgt att cca gtt tgt<br>Ser Asn Gly Asn Trp Ser Gly Arg Pro Ala Ser Cys Ile Pro Val Cys<br>         740                  745                  750 | 2256 |
| gga cgg tca gac tct cct cgt tct cct ttc atc tgg aat ggg aat tct<br>Gly Arg Ser Asp Ser Pro Arg Ser Pro Phe Ile Trp Asn Gly Asn Ser<br>755                     760                 765 | 2304 |
| aca gaa ata ggt cag tgg ccg tgg cag gca gga atc tct cga tgg ctt<br>Thr Glu Ile Gly Gln Trp Pro Trp Gln Ala Gly Ile Ser Arg Trp Leu<br>770                     775                  780 | 2352 |
| gca gac cac aat atg tgg ttt ctc cag tgt gga gga tcc cta ttg aat<br>Ala Asp His Asn Met Trp Phe Leu Gln Cys Gly Gly Ser Leu Leu Asn<br>785                     790                  795               800 | 2400 |
| gag aaa tgg atc gtc act gct gcc cac tgt gtc acc tac tct gct act<br>Glu Lys Trp Ile Val Thr Ala Ala His Cys Val Thr Tyr Ser Ala Thr<br>                   805                  810               815 | 2448 |
| gct gag ata att gat ccc agt cag ttt aaa atc tat ctg ggc aag tac<br>Ala Glu Ile Ile Asp Pro Ser Gln Phe Lys Ile Tyr Leu Gly Lys Tyr<br>                   820                  825               830 | 2496 |
| tac cgt gat gac agt aga gac gat gac tac gta caa gta aga gag gct<br>Tyr Arg Asp Asp Ser Arg Asp Asp Asp Tyr Val Gln Val Arg Glu Ala<br>835                     840                  845 | 2544 |
| ctc gag atc cac gta aat cct aac tac gac ccc ggc aat ctc aac ttt<br>Leu Glu Ile His Val Asn Pro Asn Tyr Asp Pro Gly Asn Leu Asn Phe<br>850                     855                  860 | 2592 |
| gac ata gcc cta att caa ctg aaa act cct gtt act ttg aca aca cga<br>Asp Ile Ala Leu Ile Gln Leu Lys Thr Pro Val Thr Leu Thr Thr Arg<br>865                     870                  875               880 | 2640 |
| gtc caa cca atc tgt ctg cct act gac atc aca aca aga gaa cac ttg<br>Val Gln Pro Ile Cys Leu Pro Thr Asp Ile Thr Thr Arg Glu His Leu<br>                   885                  890               895 | 2688 |
| aag gag gga aca tta gca gtg gtg aca ggt tgg ggt ttg aat gaa aac<br>Lys Glu Gly Thr Leu Ala Val Val Thr Gly Trp Gly Leu Asn Glu Asn<br>                   900                  905               910 | 2736 |
| aac aca tat tca gag atg att caa caa gct gtg cta cct gtt gtt gca<br>Asn Thr Tyr Ser Glu Met Ile Gln Gln Ala Val Leu Pro Val Val Ala<br>         915                  920                  925 | 2784 |
| gca agc acc tgt gaa gag ggg tac aag gaa gca gac tta cca ctg aca<br>Ala Ser Thr Cys Glu Glu Gly Tyr Lys Glu Ala Asp Leu Pro Leu Thr<br>930                     935                  940 | 2832 |
| gta aca gag aac atg ttc tgt gca ggt tac aag aag gga cgt tat gat<br>Val Thr Glu Asn Met Phe Cys Ala Gly Tyr Lys Lys Gly Arg Tyr Asp<br>945                     950                  955               960 | 2880 |
| gcc tgc agt ggg gac agt gga gga cca tta gtg ttt gct gat gat tcc<br>Ala Cys Ser Gly Asp Ser Gly Gly Pro Leu Val Phe Ala Asp Asp Ser<br>                   965                  970               975 | 2928 |
| cgt acc gaa agg cgg tgg gtc ttg gaa ggg att gtc agc tgg ggc agt<br>Arg Thr Glu Arg Arg Trp Val Leu Glu Gly Ile Val Ser Trp Gly Ser<br>                   980                  985               990 | 2976 |
| ccc agt gga tgt ggc aag gct aac cag tat ggg ggc ttc act aaa gtt<br>Pro Ser Gly Cys Gly Lys Ala Asn Gln Tyr Gly Gly Phe Thr Lys Val | 3024 |

```
                995            1000              1005
aac  gtt  ttt  cta  tca  tgg  att  agg  cag  ttc  att  tga          3060
Asn  Val  Phe  Leu  Ser  Trp  Ile  Arg  Gln  Phe  Ile
     1010                     1015
```

<210> SEQ ID NO 2
<211> LENGTH: 1019
<212> TYPE: PRT
<213> ORGANISM: Tachypleus tridentatus

<400> SEQUENCE: 2

```
Met Val Leu Ala Ser Phe Leu Val Ser Gly Leu Val Leu Gly Ile Leu
1               5                   10                  15

Ala Gln Gln Met Arg Pro Val Gln Ser Arg Gly Val Asp Leu Gly Leu
            20                  25                  30

Cys Asp Glu Thr Arg Phe Glu Cys Lys Cys Gly Asp Pro Gly Tyr Val
        35                  40                  45

Phe Asn Val Pro Met Lys Gln Cys Thr Tyr Phe Tyr Arg Trp Arg Pro
    50                  55                  60

Tyr Cys Lys Pro Cys Asp Asp Leu Glu Ala Lys Asp Ile Cys Pro Lys
65                  70                  75                  80

Tyr Lys Arg Cys Gln Glu Cys Lys Ala Gly Leu Asp Ser Cys Val Thr
                85                  90                  95

Cys Pro Pro Asn Lys Tyr Gly Thr Trp Cys Ser Gly Glu Cys Gln Cys
            100                 105                 110

Lys Asn Gly Gly Ile Cys Asp Gln Arg Thr Gly Ala Cys Thr Cys Arg
        115                 120                 125

Asp Arg Tyr Glu Gly Ala His Cys Glu Ile Leu Lys Gly Cys Pro Leu
    130                 135                 140

Leu Pro Ser Asp Ser Gln Val Gln Glu Val Arg Asn Pro Pro Asp Asn
145                 150                 155                 160

Pro Gln Thr Ile Asp Tyr Ser Cys Ser Pro Gly Phe Lys Leu Lys Gly
                165                 170                 175

Val Ala Arg Ile Ser Cys Leu Pro Asn Gly Gln Trp Ser Ser Phe Pro
            180                 185                 190

Pro Lys Cys Ile Arg Glu Cys Ala Lys Val Ser Ser Pro Glu His Gly
        195                 200                 205

Lys Val Asn Ala Pro Ser Gly Asn Met Ile Glu Gly Ala Thr Leu Arg
    210                 215                 220

Phe Ser Cys Asp Ser Pro Tyr Tyr Leu Ile Gly Gln Glu Thr Leu Thr
225                 230                 235                 240

Cys Gln Gly Asn Gly Gln Trp Ser Gly Gln Ile Pro Gln Cys Lys Lys
                245                 250                 255

Leu Val Phe Cys Pro Asp Leu Asp Pro Val Asn His Ala Glu His Gln
            260                 265                 270

Val Lys Ile Gly Val Glu Gln Lys Tyr Gly Gln Phe Pro Gln Gly Thr
        275                 280                 285

Glu Val Thr Tyr Thr Cys Ser Gly Asn Tyr Phe Leu Met Gly Phe Asn
    290                 295                 300

Thr Leu Lys Cys Asn Pro Asp Gly Ser Trp Ser Gly Ser Gln Pro Ser
305                 310                 315                 320

Cys Val Lys Val Ala Asp Arg Glu Val Asp Cys Asp Ser Lys Ala Val
                325                 330                 335

Asp Phe Leu Asp Asp Val Gly Glu Pro Val Arg Ile His Cys Pro Ala
            340                 345                 350
```

-continued

```
Gly Cys Ser Leu Thr Ala Gly Thr Val Trp Gly Thr Ala Ile Tyr His
            355                 360                 365
Glu Leu Ser Ser Val Cys Arg Ala Ala Ile His Ala Gly Lys Leu Pro
    370                 375                 380
Asn Ser Gly Gly Ala Val His Val Val Asn Asn Gly Pro Tyr Ser Asp
385                 390                 395                 400
Phe Leu Gly Ser Asp Leu Asn Gly Ile Lys Ser Glu Glu Leu Lys Ser
                405                 410                 415
Leu Ala Arg Ser Phe Arg Phe Asp Tyr Val Ser Ser Thr Ala Gly
            420                 425                 430
Arg Ser Gly Cys Pro Asp Gly Trp Phe Glu Val Glu Asn Cys Val
            435                 440                 445
Tyr Val Thr Ser Lys Gln Arg Ala Trp Glu Arg Ala Gln Gly Val Cys
    450                 455                 460
Thr Asn Met Ala Ala Arg Leu Ala Val Leu Asp Lys Asp Leu Ile Pro
465                 470                 475                 480
Ser Ser Leu Thr Glu Thr Leu Arg Gly Lys Gly Leu Thr Thr Thr Trp
                485                 490                 495
Ile Gly Leu His Arg Leu Asp Ala Glu Lys Pro Phe Val Trp Glu Leu
                500                 505                 510
Met Asp Arg Ser Asn Val Val Leu Asn Asp Asn Leu Thr Phe Trp Ala
            515                 520                 525
Ser Gly Glu Pro Gly Asn Glu Thr Asn Cys Val Tyr Leu Asp Ile Arg
    530                 535                 540
Asp Gln Leu Gln Pro Val Trp Lys Thr Lys Ser Cys Phe Gln Pro Ser
545                 550                 555                 560
Ser Phe Ala Cys Met Met Asp Leu Ser Asp Arg Asn Lys Ala Lys Cys
                565                 570                 575
Asp Asp Pro Gly Pro Leu Glu Asn Gly His Ala Thr Leu His Gly Gln
            580                 585                 590
Ser Ile Asp Gly Phe Tyr Ala Gly Ser Ser Ile Arg Tyr Ser Cys Glu
    595                 600                 605
Val Leu His Tyr Leu Ser Gly Thr Glu Thr Val Thr Cys Thr Thr Asn
    610                 615                 620
Gly Thr Trp Ser Ala Pro Lys Pro Arg Cys Ile Lys Val Ile Thr Cys
625                 630                 635                 640
Gln Asn Pro Pro Val Pro Ser Tyr Gly Ser Val Glu Ile Lys Pro Pro
                645                 650                 655
Ser Arg Thr Asn Ser Ile Ser Arg Val Gly Ser Pro Phe Leu Arg Leu
            660                 665                 670
Pro Arg Leu Pro Leu Pro Leu Ala Arg Ala Lys Pro Pro Lys
            675                 680                 685
Pro Arg Ser Ser Gln Pro Ser Thr Val Asp Leu Ala Ser Lys Val Lys
    690                 695                 700
Leu Pro Glu Gly His Tyr Arg Val Gly Ser Arg Ala Ile Tyr Thr Cys
705                 710                 715                 720
Glu Ser Arg Tyr Tyr Glu Leu Leu Gly Ser Gln Gly Arg Arg Cys Asp
                725                 730                 735
Ser Asn Gly Asn Trp Ser Gly Arg Pro Ala Ser Cys Ile Pro Val Cys
            740                 745                 750
Gly Arg Ser Asp Ser Pro Arg Ser Pro Phe Ile Trp Asn Gly Asn Ser
            755                 760                 765
```

```
Thr Glu Ile Gly Gln Trp Pro Trp Gln Ala Gly Ile Ser Arg Trp Leu
    770             775                 780
Ala Asp His Asn Met Trp Phe Leu Gln Cys Gly Gly Ser Leu Leu Asn
785                 790                 795                 800
Glu Lys Trp Ile Val Thr Ala Ala His Cys Val Thr Tyr Ser Ala Thr
                805                 810                 815
Ala Glu Ile Ile Asp Pro Ser Gln Phe Lys Ile Tyr Leu Gly Lys Tyr
            820                 825                 830
Tyr Arg Asp Asp Ser Arg Asp Asp Tyr Val Gln Val Arg Glu Ala
        835                 840                 845
Leu Glu Ile His Val Asn Pro Asn Tyr Asp Pro Gly Asn Leu Asn Phe
850                 855                 860
Asp Ile Ala Leu Ile Gln Leu Lys Thr Pro Val Thr Leu Thr Thr Arg
865                 870                 875                 880
Val Gln Pro Ile Cys Leu Pro Thr Asp Ile Thr Arg Glu His Leu
                885                 890                 895
Lys Glu Gly Thr Leu Ala Val Val Thr Gly Trp Gly Leu Asn Glu Asn
            900                 905                 910
Asn Thr Tyr Ser Glu Met Ile Gln Gln Ala Val Leu Pro Val Val Ala
        915                 920                 925
Ala Ser Thr Cys Glu Glu Gly Tyr Lys Glu Ala Asp Leu Pro Leu Thr
    930                 935                 940
Val Thr Glu Asn Met Phe Cys Ala Gly Tyr Lys Lys Gly Arg Tyr Asp
945                 950                 955                 960
Ala Cys Ser Gly Asp Ser Gly Gly Pro Leu Val Phe Ala Asp Ser
                965                 970                 975
Arg Thr Glu Arg Arg Trp Val Leu Glu Gly Ile Val Ser Trp Gly Ser
            980                 985                 990
Pro Ser Gly Cys Gly Lys Ala Asn Gln Tyr Gly Gly Phe Thr Lys Val
        995                 1000                1005
Asn Val Phe Leu Ser Trp Ile Arg Gln Phe Ile
    1010                1015

<210> SEQ ID NO 3
<211> LENGTH: 1203
<212> TYPE: DNA
<213> ORGANISM: Tachypleus tridentatus
<220> FEATURE:
<221> NAME/KEY: CDS
<222> LOCATION: (1)..(1203)

<400> SEQUENCE: 3 atg acg tgg ata tgt gtg ata acg ttg ttt gct ctg gct tct gct acg      48
Met Thr Trp Ile Cys Val Ile Thr Leu Phe Ala Leu Ala Ser Ala Thr
1               5                   10                  15 ttg ggt aac aaa gtt agt aga gtg ggg gtc ctc ttc ccc aag aca cgg     96
Leu Gly Asn Lys Val Ser Arg Val Gly Val Leu Phe Pro Lys Thr Arg
            20                  25                  30 aac gac aat gag tgt aca gca aga ggg gga ttg aaa gga tcc tgc aaa    144
Asn Asp Asn Glu Cys Thr Ala Arg Gly Gly Leu Lys Gly Ser Cys Lys
        35                  40                  45 tcc ctc ata gac tgt cct agt gtc ttg gct acg ttg aag gac agt ttt    192
Ser Leu Ile Asp Cys Pro Ser Val Leu Ala Thr Leu Lys Asp Ser Phe
    50                  55                  60 cct gtc gtt tgc tct tgg aat ggt cga ttt cag cct att gtc tgc tgt    240
Pro Val Val Cys Ser Trp Asn Gly Arg Phe Gln Pro Ile Val Cys Cys
65                  70                  75                  80
```

-continued

| | | |
|---|---|---|
| cct gat gca ata gca cca cca cct gta acc aca aca gct gta act gta<br>Pro Asp Ala Ile Ala Pro Pro Pro Val Thr Thr Thr Ala Val Thr Val<br>                          85                    90                  95 | 288 |
| ata tct aca aaa gaa cca aag ctt cca aga tta cat ata tca ggt tgt<br>Ile Ser Thr Lys Glu Pro Lys Leu Pro Arg Leu His Ile Ser Gly Cys<br>                100                  105                  110 | 336 |
| gga aaa aga aaa gtc aaa ata gat att aca act gtt gga cgc tct gga<br>Gly Lys Arg Lys Val Lys Ile Asp Ile Thr Thr Val Gly Arg Ser Gly<br>              115                  120                  125 | 384 |
| tca cca ata ctt cct ccg ata tct act cct caa aat tca aca ggt ggg<br>Ser Pro Ile Leu Pro Pro Ile Ser Thr Pro Gln Asn Ser Thr Gly Gly<br>      130                  135                  140 | 432 |
| aga gga att att gct gga ggc gta gaa gcc aaa att ggc gcg tgg cct<br>Arg Gly Ile Ile Ala Gly Gly Val Glu Ala Lys Ile Gly Ala Trp Pro<br>145                    150                  155                  160 | 480 |
| tgg atg gca gct gtt ttt gtg aaa aac ttt ggc att ggc aga ttc cac<br>Trp Met Ala Ala Val Phe Val Lys Asn Phe Gly Ile Gly Arg Phe His<br>                  165                  170                  175 | 528 |
| tgt gct ggt agc ata atc agt aac aag tac att ttg tca gct gcc cac<br>Cys Ala Gly Ser Ile Ile Ser Asn Lys Tyr Ile Leu Ser Ala Ala His<br>                180                  185                  190 | 576 |
| gcc ttc ctt atc gga ggt cga aag ttg acc cca act cgc tta gct gtc<br>Ala Phe Leu Ile Gly Gly Arg Lys Leu Thr Pro Thr Arg Leu Ala Val<br>            195                  200                  205 | 624 |
| cgt gtg gga ggc cac tac ata aag agg ggt caa gag tat cca gtg aaa<br>Arg Val Gly Gly His Tyr Ile Lys Arg Gly Gln Glu Tyr Pro Val Lys<br>      210                  215                  220 | 672 |
| gac gtg att atc cat cct cat tat gta gaa aag gag aac tac aat gat<br>Asp Val Ile Ile His Pro His Tyr Val Glu Lys Glu Asn Tyr Asn Asp<br>225                    230                  235                  240 | 720 |
| ata gcc ata atc gag tta aaa gag gaa ctg aac ttt acg gac ttg gtc<br>Ile Ala Ile Ile Glu Leu Lys Glu Glu Leu Asn Phe Thr Asp Leu Val<br>                  245                  250                  255 | 768 |
| aat cct ata tgt ctc cct gat cca gag aca gta acg gat cca tta aaa<br>Asn Pro Ile Cys Leu Pro Asp Pro Glu Thr Val Thr Asp Pro Leu Lys<br>                260                  265                  270 | 816 |
| gac aga att gtg act gca gcg gga tgg ggc gat ctg gat ttc tcc ggt<br>Asp Arg Ile Val Thr Ala Ala Gly Trp Gly Asp Leu Asp Phe Ser Gly<br>            275                  280                  285 | 864 |
| cca cgg agc caa gtt cta cgt gag gta agc atc cca gtt gtt cca gtt<br>Pro Arg Ser Gln Val Leu Arg Glu Val Ser Ile Pro Val Val Pro Val<br>      290                  295                  300 | 912 |
| gat aaa tgt gat caa gcc tat gag aaa ctc aac acc cct tca cta aaa<br>Asp Lys Cys Asp Gln Ala Tyr Glu Lys Leu Asn Thr Pro Ser Leu Lys<br>305                    310                  315                  320 | 960 |
| aat ggg ata acg aat aac ttc ctt tgc gct gga ttg gaa gaa gga ggg<br>Asn Gly Ile Thr Asn Asn Phe Leu Cys Ala Gly Leu Glu Glu Gly Gly<br>                  325                  330                  335 | 1008 |
| aaa gac gct tgc caa ggc gat tct ggt gga ccg ttg atg cta gtg aac<br>Lys Asp Ala Cys Gln Gly Asp Ser Gly Gly Pro Leu Met Leu Val Asn<br>                340                  345                  350 | 1056 |
| aac act agg tgg ata gta gta gga gtt gtg tcg ttc ggg cac aag tgt<br>Asn Thr Arg Trp Ile Val Val Gly Val Val Ser Phe Gly His Lys Cys<br>            355                  360                  365 | 1104 |
| gcc gag gaa gga tat cct ggt gtg tac tcg cgc gta gcg agt tac cta<br>Ala Glu Glu Gly Tyr Pro Gly Val Tyr Ser Arg Val Ala Ser Tyr Leu<br>      370                  375                  380 | 1152 |
| gac tgg atc gcg aaa gtt acg aac tcg tta gat cat gcc gtc act aac<br>Asp Trp Ile Ala Lys Val Thr Asn Ser Leu Asp His Ala Val Thr Asn<br>385                    390                  395                  400 | 1200 |

```
taa                                                                1203
```

<210> SEQ ID NO 4
<211> LENGTH: 400
<212> TYPE: PRT
<213> ORGANISM: Tachypleus tridentatus

<400> SEQUENCE: 4

```
Met Thr Trp Ile Cys Val Ile Thr Leu Phe Ala Leu Ala Ser Ala Thr
1               5                   10                  15

Leu Gly Asn Lys Val Ser Arg Val Gly Val Leu Phe Pro Lys Thr Arg
            20                  25                  30

Asn Asp Asn Glu Cys Thr Ala Arg Gly Gly Leu Lys Gly Ser Cys Lys
        35                  40                  45

Ser Leu Ile Asp Cys Pro Ser Val Leu Ala Thr Leu Lys Asp Ser Phe
50                  55                  60

Pro Val Val Cys Ser Trp Asn Gly Arg Phe Gln Pro Ile Val Cys Cys
65                  70                  75                  80

Pro Asp Ala Ile Ala Pro Pro Val Thr Thr Ala Val Thr Val
                85                  90                  95

Ile Ser Thr Lys Glu Pro Lys Leu Pro Arg Leu His Ile Ser Gly Cys
                100                 105                 110

Gly Lys Arg Lys Val Lys Ile Asp Ile Thr Thr Val Gly Arg Ser Gly
            115                 120                 125

Ser Pro Ile Leu Pro Pro Ile Ser Thr Pro Gln Asn Ser Thr Gly Gly
        130                 135                 140

Arg Gly Ile Ile Ala Gly Gly Val Glu Ala Lys Ile Gly Ala Trp Pro
145                 150                 155                 160

Trp Met Ala Ala Val Phe Val Lys Asn Phe Gly Ile Gly Arg Phe His
                165                 170                 175

Cys Ala Gly Ser Ile Ile Ser Asn Lys Tyr Ile Leu Ser Ala Ala His
            180                 185                 190

Ala Phe Leu Ile Gly Gly Arg Lys Leu Thr Pro Thr Arg Leu Ala Val
        195                 200                 205

Arg Val Gly Gly His Tyr Ile Lys Arg Gly Gln Glu Tyr Pro Val Lys
    210                 215                 220

Asp Val Ile Ile His Pro His Tyr Val Glu Lys Glu Asn Tyr Asn Asp
225                 230                 235                 240

Ile Ala Ile Ile Glu Leu Lys Glu Leu Asn Phe Thr Asp Leu Val
                245                 250                 255

Asn Pro Ile Cys Leu Pro Asp Pro Glu Thr Val Thr Asp Pro Leu Lys
                260                 265                 270

Asp Arg Ile Val Thr Ala Ala Gly Trp Gly Asp Leu Asp Phe Ser Gly
            275                 280                 285

Pro Arg Ser Gln Val Leu Arg Glu Val Ser Ile Pro Val Val Pro Val
        290                 295                 300

Asp Lys Cys Asp Gln Ala Tyr Glu Lys Leu Asn Thr Pro Ser Leu Lys
305                 310                 315                 320

Asn Gly Ile Thr Asn Asn Phe Leu Cys Ala Gly Leu Glu Glu Gly Gly
                325                 330                 335

Lys Asp Ala Cys Gln Gly Asp Ser Gly Gly Pro Leu Met Leu Val Asn
            340                 345                 350

Asn Thr Arg Trp Ile Val Val Gly Val Val Ser Phe Gly His Lys Cys
        355                 360                 365
```

```
Ala Glu Glu Gly Tyr Pro Gly Val Tyr Ser Arg Val Ala Ser Tyr Leu
    370                 375                 380

Asp Trp Ile Ala Lys Val Thr Asn Ser Leu Asp His Ala Val Thr Asn
385                 390                 395                 400

<210> SEQ ID NO 5
<211> LENGTH: 1128
<212> TYPE: DNA
<213> ORGANISM: Tachypleus tridentatus
<220> FEATURE:
<221> NAME/KEY: CDS
<222> LOCATION: (1)..(1128)

<400> SEQUENCE: 5
```

| | | | | | | | | | | | | | | | | |
|---|---|---|---|---|---|---|---|---|---|---|---|---|---|---|---|---|
| atg | ttg | gtg | aat | aac | gtg | ttt | tca | cta | ctg | tgt | ttc | cca | ctc | ttg | atg | 48 |
| Met | Leu | Val | Asn | Asn | Val | Phe | Ser | Leu | Leu | Cys | Phe | Pro | Leu | Leu | Met | |
| 1 | | | | 5 | | | | | 10 | | | | | 15 | | |
| tct | gtg | gtt | aga | tgc | agt | act | ctc | agc | aga | cag | cgt | aga | cag | ttt | gtt | 96 |
| Ser | Val | Val | Arg | Cys | Ser | Thr | Leu | Ser | Arg | Gln | Arg | Arg | Gln | Phe | Val | |
| | | | 20 | | | | | 25 | | | | | 30 | | | |
| ttc | cct | gac | gag | gaa | gaa | ctt | tgc | tca | aac | cga | ttt | act | gaa | gaa | gga | 144 |
| Phe | Pro | Asp | Glu | Glu | Glu | Leu | Cys | Ser | Asn | Arg | Phe | Thr | Glu | Glu | Gly | |
| | | 35 | | | | | 40 | | | | | 45 | | | | |
| aca | tgc | aaa | aat | gtc | ttg | gat | tgt | aga | ata | ctt | tta | caa | aaa | aat | gat | 192 |
| Thr | Cys | Lys | Asn | Val | Leu | Asp | Cys | Arg | Ile | Leu | Leu | Gln | Lys | Asn | Asp | |
| | 50 | | | | | 55 | | | | | 60 | | | | | |
| tat | aat | tta | ctc | aaa | gaa | tca | ata | tgc | ggc | ttt | gaa | ggc | ata | aca | ccc | 240 |
| Tyr | Asn | Leu | Leu | Lys | Glu | Ser | Ile | Cys | Gly | Phe | Glu | Gly | Ile | Thr | Pro | |
| 65 | | | | | 70 | | | | | 75 | | | | | 80 | |
| aaa | gtt | tgt | tgt | ccg | aaa | tca | agc | cat | gta | att | tca | agt | aca | cag | gca | 288 |
| Lys | Val | Cys | Cys | Pro | Lys | Ser | Ser | His | Val | Ile | Ser | Ser | Thr | Gln | Ala | |
| | | | | 85 | | | | | 90 | | | | | 95 | | |
| cct | cca | gaa | acc | act | acg | act | gaa | cgc | cca | cca | aaa | cag | ata | cca | ccc | 336 |
| Pro | Pro | Glu | Thr | Thr | Thr | Thr | Glu | Arg | Pro | Pro | Lys | Gln | Ile | Pro | Pro | |
| | | | 100 | | | | | 105 | | | | | 110 | | | |
| aat | ctt | cat | gaa | gtg | tgt | gga | att | cac | aat | act | aca | act | acc | agg | att | 384 |
| Asn | Leu | His | Glu | Val | Cys | Gly | Ile | His | Asn | Thr | Thr | Thr | Thr | Arg | Ile | |
| | | 115 | | | | | 120 | | | | | 125 | | | | |
| att | gga | ggt | cgg | gaa | gca | cct | att | gga | gcc | tgg | ccg | tgg | atg | act | gct | 432 |
| Ile | Gly | Gly | Arg | Glu | Ala | Pro | Ile | Gly | Ala | Trp | Pro | Trp | Met | Thr | Ala | |
| | 130 | | | | | 135 | | | | | 140 | | | | | |
| gtc | tac | ata | aaa | caa | gga | gga | atc | aga | agt | gtt | cag | tgt | ggt | ggc | gca | 480 |
| Val | Tyr | Ile | Lys | Gln | Gly | Gly | Ile | Arg | Ser | Val | Gln | Cys | Gly | Gly | Ala | |
| 145 | | | | | 150 | | | | | 155 | | | | | 160 | |
| ctt | gtc | act | aac | agg | cac | gtg | att | aca | gct | tcg | cac | tgt | gtt | gta | aac | 528 |
| Leu | Val | Thr | Asn | Arg | His | Val | Ile | Thr | Ala | Ser | His | Cys | Val | Val | Asn | |
| | | | | 165 | | | | | 170 | | | | | 175 | | |
| agt | gca | gga | aca | gat | gtg | atg | cca | gct | gat | gta | ttc | tcg | gtt | cgt | ctg | 576 |
| Ser | Ala | Gly | Thr | Asp | Val | Met | Pro | Ala | Asp | Val | Phe | Ser | Val | Arg | Leu | |
| | | | 180 | | | | | 185 | | | | | 190 | | | |
| ggt | gaa | cac | aat | tta | tac | agt | acc | gat | gac | gat | tcg | aat | cca | ata | gat | 624 |
| Gly | Glu | His | Asn | Leu | Tyr | Ser | Thr | Asp | Asp | Asp | Ser | Asn | Pro | Ile | Asp | |
| | | 195 | | | | | 200 | | | | | 205 | | | | |
| ttt | gca | gtt | acg | tcg | gtg | aaa | cat | cac | gaa | cac | ttt | gta | ctc | gcg | acg | 672 |
| Phe | Ala | Val | Thr | Ser | Val | Lys | His | His | Glu | His | Phe | Val | Leu | Ala | Thr | |
| | 210 | | | | | 215 | | | | | 220 | | | | | |
| tat | ttg | aat | gac | atc | gca | att | cta | acg | tta | aat | gac | aca | gtt | acg | ttt | 720 |
| Tyr | Leu | Asn | Asp | Ile | Ala | Ile | Leu | Thr | Leu | Asn | Asp | Thr | Val | Thr | Phe | |
| 225 | | | | | 230 | | | | | 235 | | | | | 240 | |
| aca | gac | aga | att | cga | ccc | att | tgt | cta | cct | tat | cgt | aag | ttg | aga | tac | 768 |

-continued

```
                    Thr Asp Arg Ile Arg Pro Ile Cys Leu Pro Tyr Arg Lys Leu Arg Tyr
                                    245                 250                 255 gat gat cta gca atg aga aaa ccg ttt atc act gga tgg gga aca aca           816
Asp Asp Leu Ala Met Arg Lys Pro Phe Ile Thr Gly Trp Gly Thr Thr
                260                 265                 270 gca ttt aac ggc cca tct agt gca gtg ttg aga gaa gta cag tta cca           864
Ala Phe Asn Gly Pro Ser Ser Ala Val Leu Arg Glu Val Gln Leu Pro
                275                 280                 285 ata tgg gaa cac gag gcc tgt aga cag gcc tac gag aag gat tta aat           912
Ile Trp Glu His Glu Ala Cys Arg Gln Ala Tyr Glu Lys Asp Leu Asn
            290                 295                 300 att aca aac gtg tat atg tgt gct ggc ttt gca gat ggc ggg aag gat           960
Ile Thr Asn Val Tyr Met Cys Ala Gly Phe Ala Asp Gly Gly Lys Asp
305                 310                 315                 320 gct tgc cag ggt gat tct gga ggt cca atg atg ttg cct gtt aaa acc          1008
Ala Cys Gln Gly Asp Ser Gly Gly Pro Met Met Leu Pro Val Lys Thr
                325                 330                 335 gga gag ttt tat ctc att gga att gtg tct ttc gga aag aaa tgc gca          1056
Gly Glu Phe Tyr Leu Ile Gly Ile Val Ser Phe Gly Lys Lys Cys Ala
                340                 345                 350 ttg cct gga ttt cct ggg gtt tac aca aaa gtg aca gag ttt tta gat          1104
Leu Pro Gly Phe Pro Gly Val Tyr Thr Lys Val Thr Glu Phe Leu Asp
                355                 360                 365 tgg att gca gaa cat atg gtg tag                                          1128
Trp Ile Ala Glu His Met Val
                370                 375
```

<210> SEQ ID NO 6
<211> LENGTH: 375
<212> TYPE: PRT
<213> ORGANISM: Tachypleus tridentatus

<400> SEQUENCE: 6

```
Met Leu Val Asn Asn Val Phe Ser Leu Leu Cys Phe Pro Leu Leu Met
1               5                   10                  15

Ser Val Val Arg Cys Ser Thr Leu Ser Arg Gln Arg Gln Phe Val
                20                  25                  30

Phe Pro Asp Glu Glu Leu Cys Ser Asn Arg Phe Thr Glu Glu Gly
                35                  40                  45

Thr Cys Lys Asn Val Leu Asp Cys Arg Ile Leu Leu Gln Lys Asn Asp
            50                  55                  60

Tyr Asn Leu Leu Lys Glu Ser Ile Cys Gly Phe Glu Gly Ile Thr Pro
65              70                  75                  80

Lys Val Cys Cys Pro Lys Ser Ser His Val Ile Ser Thr Gln Ala
                85                  90                  95

Pro Pro Glu Thr Thr Thr Thr Glu Arg Pro Lys Gln Ile Pro Pro
                100                 105                 110

Asn Leu His Glu Val Cys Gly Ile His Asn Thr Thr Thr Arg Ile
            115                 120                 125

Ile Gly Gly Arg Glu Ala Pro Ile Gly Ala Trp Pro Trp Met Thr Ala
                130                 135                 140

Val Tyr Ile Lys Gln Gly Gly Ile Arg Ser Val Gln Cys Gly Gly Ala
145             150                 155                 160

Leu Val Thr Asn Arg His Val Ile Thr Ala Ser His Cys Val Val Asn
                165                 170                 175

Ser Ala Gly Thr Asp Val Met Pro Ala Asp Val Phe Ser Val Arg Leu
                180                 185                 190
```

```
Gly Glu His Asn Leu Tyr Ser Thr Asp Asp Ser Asn Pro Ile Asp
            195                 200                 205

Phe Ala Val Thr Ser Val Lys His His Glu His Phe Val Leu Ala Thr
    210                 215                 220

Tyr Leu Asn Asp Ile Ala Ile Leu Thr Leu Asn Asp Thr Val Thr Phe
225                 230                 235                 240

Thr Asp Arg Ile Arg Pro Ile Cys Leu Pro Tyr Arg Lys Leu Arg Tyr
                245                 250                 255

Asp Asp Leu Ala Met Arg Lys Pro Phe Ile Thr Gly Trp Gly Thr Thr
                260                 265                 270

Ala Phe Asn Gly Pro Ser Ser Ala Val Leu Arg Glu Val Gln Leu Pro
            275                 280                 285

Ile Trp Glu His Glu Ala Cys Arg Gln Ala Tyr Glu Lys Asp Leu Asn
        290                 295                 300

Ile Thr Asn Val Tyr Met Cys Ala Gly Phe Ala Asp Gly Gly Lys Asp
305                 310                 315                 320

Ala Cys Gln Gly Asp Ser Gly Gly Pro Met Met Leu Pro Val Lys Thr
                325                 330                 335

Gly Glu Phe Tyr Leu Ile Gly Ile Val Ser Phe Gly Lys Lys Cys Ala
            340                 345                 350

Leu Pro Gly Phe Pro Gly Val Tyr Thr Lys Val Thr Glu Phe Leu Asp
        355                 360                 365

Trp Ile Ala Glu His Met Val
        370                 375

<210> SEQ ID NO 7
<211> LENGTH: 3078
<212> TYPE: DNA
<213> ORGANISM: Tachypleus tridentatus

<400> SEQUENCE: 7
atggtcttag cgtcgttttt ggtgtctggt ttagttctag ggatactagc ccaacaaatg      60
cgtccagttc agtccagagg agtagatctg ggcttgtgtg atgaaacgag gttcgagtgt     120
aagtgtggag atccaggcta tgtgttcaac gtccctatga acaatgcac gtacttctat      180 cgatggaggc cttattgtaa accatgtgat gacctggagg ctaaggacat tgtccaaag      240 tacaaacgat gtcaagagtg taaggctggt cttgatagtt gtgttacttg tccacctaac     300
aaatatggta cttggtgtag cggtgaatgt caatgtaaga atggaggtat ctgtgaccag     360
aggacaggag cttgtacctg tcgtgacaga tatgaaggag cgcactgtga aattctcaaa     420
ggttgtcctc ttcttccatc ggattctcaa gttcaggaag tcagaaaccc accagataat     480
ccccaaacta ttgactacag ctgttcacca gggttcaagc ttaaaggcgt ggcacgaatt     540
agctgtctcc caaatggaca gtggagtagc tttccaccca atgtattcg agaatgtgcc      600 aaggtttcat ctccagaaca cgggaaagtg aatgctccta gtggcaatat gatgaaggg     660 gctactttac ggttctcatg tgatagtccc tactacttga ttggtcaaga acattaacc     720 tgccagggta atggtcagtg gagtggacaa ataccacaat gtaagaagtt ggtcttctgt     780
cctgaccttg atcctgtaaa ccatgctgaa caccaggtta aaattggtgt ggaacaaaaa     840
tatggtcagt ttcctcaagg cactgaagtg acctatacgt gttcgggtaa ctacttcttg     900
atgggtttta acaccttaaa atgtaaccct gatgggtcct ggtcaggatc acagccatcc     960
tgtgttaaag tggcagacag agaggtcgac tgtgacagta aagctgtaga cttcttggat    1020
gatgttggtg aacctgtcag gatccactgt cctgctggct gttctttgac agctggtact    1080
```

| | |
|---|---|
| gtgtggggta cagccatata ccacgaactt tcctcagtgt gtcgtgcagc catccatgct | 1140 |
| ggcaagcttc caaactctgg aggggcggtg catgtagtga acaatggccc ctactcggac | 1200 |
| tttctgggta gtgacctgaa tgggataaaa tcggaagagt tgaagtctct tgcccgcagt | 1260 |
| tttcgatttg attatgtcag ttcatccaca gcaggtagta caggatgtcc tgatggatgg | 1320 |
| tttgaggtag aagagaactg tgtgtacgtt acatcaaaac agagagcctg ggaaagagct | 1380 |
| caaggtgtgt gtaccaatat ggctgctcgt cttgctgtgc tagacaaaga tctaattccg | 1440 |
| agttccttga ctgagactct acgagggaaa gggttaacaa ccacatggat aggattgcac | 1500 |
| agactagatg ctgagaagcc ctttgtttgg gagctaatgg atcgtagtaa tgtggttctg | 1560 |
| aatgataacc taacattctg ggcctctggc gaacctggaa atgaaactaa ctgtgtatat | 1620 |
| ctggacatcc gagatcagct gcagcctgtg tggaaaacca agtcatgttt tcagccctca | 1680 |
| agctttgctt gcatgatgga tttgtcagac agaaataaag ccaaatgcga tgaccctgga | 1740 |
| ccactggaaa atggacacgc cacacttcat ggacaaagta ttgatgggtt ctatgctggt | 1800 |
| tcttctataa ggtacagctg tgaggttctc cactacctca gtggaactga gaccgtaact | 1860 |
| tgtacaacaa atggcacatg gagtgctcct aaacctcgat gtatcaaagt catcacctgc | 1920 |
| caaaaccctc ctgtaccatc atatggttct gtggaaatca acccccaag tcggacaaac | 1980 |
| tcgatcagtc gtgttgggtc acctttcttg aggttgccac ggttaccct cccattagcc | 2040 |
| agagcagcca aacctcctcc aaaacctaga tcctcacaac cctctactgt ggacttggct | 2100 |
| tctaaagtta aactacctga aggtcattac cgggtagggt ctcgagccat ttacacgtgc | 2160 |
| gagtcgagat actacgaact acttggatct caaggcagaa gatgtgactc taatggaaac | 2220 |
| tggagtggtc ggcccgctag ctgtattcca gtttgtggac ggtcagactc tcctcgttct | 2280 |
| cctttcatct ggaatgggaa ttctacagaa ataggtcagt ggccgtggca ggcaggaatc | 2340 |
| tctcgatggc ttgcagacca caatatgtgg tttctccagt gtggaggatc cctattgaat | 2400 |
| gagaaatgga tcgtcactgc tgcccactgt gtcacctact ctgctactgc tgagataatt | 2460 |
| gatcccagtc agtttaaaat ctatctgggc aagtactacc gtgatgacag tagagacgat | 2520 |
| gactacgtac aagtaagaga ggctctcgag atccacgtaa atcctaacta cgaccccggc | 2580 |
| aatctcaact ttgacatagc cctaattcaa ctgaaaactc ctgttacttt gacaacacga | 2640 |
| gtccaaccaa tctgtctgcc tactgacatc acaacaagag aacacttgaa ggagggaaca | 2700 |
| ttagcagtgg tgacaggttg gggtttgaat gaaaacaaca catattcaga gatgattcaa | 2760 |
| caagctgtgc tacctgttgt tgcagcaagc acctgtgaag aggggtacaa ggaagcagac | 2820 |
| ttaccactga cagtaacaga gaacatgttc tgtgcaggtt acaagaaggg acgttatgat | 2880 |
| gcctgcagtg gggacagtgg aggaccatta gtgtttgctg atgattccg taccgaaagg | 2940 |
| cggtgggtct tggaagggat tgtcagctgg ggcagtccca gtggatgtgg caaggctaac | 3000 |
| cagtatgggg gcttcactaa agttaacgtt tttctatcat ggattaggca gttcattcat | 3060 |
| catcaccatc accattga | 3078 |

<210> SEQ ID NO 8
<211> LENGTH: 1203
<212> TYPE: DNA
<213> ORGANISM: Tachypleus tridentatus

<400> SEQUENCE: 8

| | |
|---|---|
| atgacctgga tctgcgtgat caccctgttc gctctggctt ccgctaccct gggcaacaag | 60 |

```
gtgtcccgtg tgggtgtcct gttccccaag acccgtaacg acaacgagtg caccgctcgt      120
ggtggtctga agggctcctg caagtccctg atcgactgcc cctccgtgct ggctaccctg      180
aaggactcct tccccgtcgt gtgctcctgg aacggtcgtt ccagcccat cgtgtgctgc       240
cccgacgcta tcgctccccc ccctgtgacc accaccgctg tgaccgtgat ctccaccaag      300
gagcccaagc tgccccgtct gcacatctcc ggttgcggca agcgcaaggt caagatcgac      360
atcaccaccg tgggccgttc cggttccccc atcctgcccc ccatctccac cccccagaac      420
tccactggtg gtcgtggtat catcgctggc ggtgtcgagg ctaagatcgg tgcttggccc      480
tggatggctg ctgtgttcgt gaagaacttc ggtatcggtc gcttccactg cgctggttcc      540
atcatctcca acaagtacat cctgtccgct gctcacgctt tcctcatcgg tggtcgcaag      600
ctgaccccca cccgtctggc tgtgcgtgtg ggtggtcact acatcaagcg tggccaggag      660
taccccgtca aggacgtgat catccacccc cactacgtgg agaaggagaa ctacaacgac      720
atcgccatca tcgagctgaa ggaggagctg aacttcaccg acctggtcaa ccccatctgc      780
ctgcccgacc ccgagactgt gaccgaccct ctgaaggacc gtatcgtgac cgctgctggc      840
tggggcgacc tggacttctc cggtccccgt tccaggtgc tgcgtgaggt gtccatcccc       900
gtggtgcccg tggacaagtg cgaccaggct tacgagaagc tgaacacccc ctccctgaag      960
aacggtatta ccaacaactt cctctgcgcc ggactcgagg agggtggcaa ggacgcttgc     1020
cagggcgact ccggtggtcc cctgatgctg gtcaacaaca cccgttggat cgtcgtgggt     1080
gtcgtgtcct tcggtcacaa gtgcgctgag gagggttacc ccggcgtcta ctcccgtgtg     1140
gcttcctacc tggactggat cgctaaggtc accaactccc tggaccacgc tgtcaccaac     1200
taa                                                                  1203
```

<210> SEQ ID NO 9
<211> LENGTH: 1128
<212> TYPE: DNA
<213> ORGANISM: Tachypleus tridentatus

<400> SEQUENCE: 9

```
atgctggtca acaacgtgtt ctccctgctg tgcttccccc tgctgatgtc cgtcgtgcgt       60
tgctccaccc tgtcccgtca gcgtcgtcag ttcgtgttcc ccgacgaaga ggagctgtgc      120
tccaaccgtt tcaccgagga gggcactttgc aagaacgtgc tggactgccg tatcctgctg      180
cagaagaacg actacaacct cctgaaggag tccatctgcg gtttcgaggg tatcactccc      240
aaggtctgct gccccaagtc ctcccacgtg atctccagca ccaggctcc ccccgagact       300
accaccaccg agcgtccccc caagcagatc ccccccaacc tccacgaggt ctgcggtatc      360
cacaacacca ccaccacccg tatcatcggt ggtcgcgagg ctcccatcgg tgcttggccc      420
tggatgaccg ctgtgtacat caagcagggt ggtatccgtt ccgtgcagtg cggaggtgct      480
ctggtcacca accgtcacgt gatcaccgct tccactgcg tggtcaactc cgctggcacc       540
gacgtgatgc ccgctgacgt gttctctgtg cgtctgggcg agcacaacct gtactccacc      600
gacgacgact ccaacccctat cgacttcgct gtgacctccg tgaagcacca cgagcacttc     660
gtgctggcta cctacctgaa cgacatcgct atcctgactc tgaacgacac cgtgaccttc      720
accgaccgta tccgtcccat ctgcctgccc taccgcaagc tgcgttacga cgacctggct     780
atgcgcaagc ccttcatcac cggctgggg caccaccgctt tcaacggtcc ctcctccgct       840
gtgctgcgtg aggtgcagct gcccatctgg gagcacgagg cttgccgtca ggcttacgag      900
aaggacctga acatcaccaa cgtgtacatg tgcgctggtt tcgctgacgg tggcaaggac      960
```

```
gcttgccagg gcgactccgg tggtcccatg atgctgcccg tcaagaccgg cgagttctac    1020
ctgatcggta tcgtgtcctt cggcaagaag tgcgctctgc ccggtttccc cggtgtctac    1080
accaaggtca ccgagttcct cgactggatc gccgagcaca tggtgtaa                1128

<210> SEQ ID NO 10
<211> LENGTH: 30
<212> TYPE: DNA
<213> ORGANISM: Artificial Sequence
<220> FEATURE:
<223> OTHER INFORMATION: primerFC-N-Pst

<400> SEQUENCE: 10
caactgcaga tggtcttagc gtcgtttttg                                    30

<210> SEQ ID NO 11
<211> LENGTH: 33
<212> TYPE: DNA
<213> ORGANISM: Artificial Sequence
<220> FEATURE:
<223> OTHER INFORMATION: primerFC-notag-R-Bam

<400> SEQUENCE: 11
caggatcctc aaatgaactg cctaatccat gat                                33

<210> SEQ ID NO 12
<211> LENGTH: 4
<212> TYPE: PRT
<213> ORGANISM: Artificial Sequence
<220> FEATURE:
<223> OTHER INFORMATION: synthesized peptide

<400> SEQUENCE: 12

Ile Glu Gly Arg
1
```

METHOD FOR PRODUCING FACTOR C RECOMBINANT PROTEIN AND ENDOTOXIN-MEASURING AGENT

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

REFERENCE TO SEQUENCE LISTING

This application incorporates by reference the sequence listing submitted as ASCII text filed via EFS-Web on Sep. 9, 2013, in U.S. application Ser. No. 14/001,138. The Sequence Listing was provided as a file entitled "2013-09-09-seq 1st toya117-021apc," created on Sep. 9, 2013, and is approximately 47 kilobytes in size.

BACKGROUND OF THE INVENTION

Field of the Invention

The present invention relates to an endotoxin-measuring agent, a method for producing the measuring agent, and a method for measuring endotoxin in a sample.

Description of the Related Art

Endotoxin is a lipopolysaccharide existing on the outer membrane of the cell wall of Gram-negative bacteria, and known to be a strong pyrogen. Further, it is known that even a small amount of endotoxin causes various disease states due to bacterial infection, such as release of inflammatory cytokines due to macrophage activation and induction of endotoxin shock, in addition to fever. Therefore, detection of endotoxin in pharmaceuticals such as those for injection; water; medical equipments; and the like is important. Further, endotoxin is considered to be the main cause of shock in Gram-negative bacterial infection, and hence, the presence or absence of infection and/or a pharmaceutical effect can be judged by measuring endotoxin in the blood.

Further, it is known that infection of American horseshoe crab (*Limulus polyphemus*) with Gram-negative bacteria causes intravascular coagulation, and this phenomenon has been used for detection of endotoxin.

That is, a method for measuring endotoxin using a blood cell extract of a horseshoe crab (horseshoe crab amebocyte lysate; hereinafter also referred to as "lysate") is known (e.g., Non-patent Document 1). This method is called "limulus test", and uses a cascade reaction of various proteins existing in the lysate, which reaction is caused by contacting of endotoxin with the lysate. A schematic diagram of the cascade reaction is shown in FIG. 1.

Upon contacting of endotoxin with the lysate, factor C existing in the lysate is activated to produce active-type factor C. This active-type factor C activates factor B existing in the lysate, to produce active-type factor B. This active-type factor B then activates a proclotting enzyme existing in the lysate, to produce a clotting enzyme.

This clotting enzyme hydrolyzes a specific portion in the coagulogen molecule existing in the lysate. By this, coagulin gel is produced, to cause coagulation of the lysate. Thus, by measuring the coagulation reaction of the lysate, endotoxin can be measured.

Further, also by allowing a clotting enzyme to react with a synthetic substrate to cause color reaction, endotoxin can be measured. For example, a clotting enzyme reacts with a synthetic substrate t-butoxycarbonyl-leucyl-glycyl-arginyl-pNA (Boc-Leu-Gly-Arg-pNA) to hydrolyze its amide bond, and thereby pNA is released. Thus, by preliminarily including the synthetic substrate in the reaction system, endotoxin can be quantified by measurement of the absorbance (405 nm) of the coloring substance (pNA).

Further, it is known that the cascade reaction system can be reconstructed using factor C, factor B, and a proclotting enzyme, which were purified from lysate of a Japanese horseshoe crab (Non-patent Document 2).

Further, a case wherein a recombinant factor C derived from a Southeast Asian horseshoe crab *Carcinoscorpius rotundicauda*; and a recombinant factor B and a recombinant proclotting enzyme derived from a Japanese horseshoe crab *Tachypleus tridentatus*; were used to reconstruct the cascade reaction system is known (Patent Document 1).

Further, a system for detecting endotoxin by using a recombinant factor C derived from a Southeast Asian horseshoe crab *Carcinoscorpius rotundicauda* and a substrate that reacts with active-type factor C to release a fluorescent substance is known (Patent Document 2). This system is commercially available as an endotoxin detection system (commercial name: PyroGene (registered trademark); Lonza).

However, in order to use the lysate, or the naturally occurring factor C, factor B, and proclotting enzyme prepared therefrom, it is necessary to capture horseshoe crabs and collect blood therefrom. Hence, in view of conservation of biological resources or the like, it is difficult to supply these components unlimitedly. Therefore, a technique to easily and rapidly produce a reagent for detection of endotoxin at a low cost has been demanded.

Further, in cases where a recombinant factor C, recombinant factor B, and recombinant proclotting enzyme are used, any of the above-described cases requires 1 hour or more for the measurement, and a detection sensitivity in the order of 0.001 EU/mL has not been achieved. Therefore, a technique to rapidly and highly sensitively measure endotoxin has been demanded.

PRIOR ART DOCUMENTS

Patent Documents

[Patent Document 1] WO 2008/004674
[Patent Document 2] U.S. Pat. No. 6,849,426 B

Non-Patent Documents

[Non-patent Document 1] Iwanaga S., Curr Opin Immunol. 1993 February; 5(1): 74-82.
[Non-patent Document 2] Nakamura T. et al., J Biochem. 1986 March; 99(3): 847-57.

SUMMARY OF THE INVENTION

The present invention aims to provide a method for rapidly and highly sensitively measuring endotoxin. The present invention also aims to provide an endotoxin-measuring agent to be used in the method, and a method for producing the agent.

The present inventors discovered that endotoxin can be rapidly and highly sensitively measured by using a recombinant factor C (His-tag free), recombinant factor B and recombinant proclotting enzyme, which were derived from a Japanese horseshoe crab *Tachypleus tridentatus* and expressed using insect cells as a host, thereby completing the present invention.

That is, the present invention is as follows.

[1]

An endotoxin-measuring agent comprising the proteins (1) to (3) below, each of which is a recombinant protein obtainable by being expressed using insect cells as a host:
  (1) a factor C derived from *Tachypleus tridentatus*, which factor C does not have His-tag sequence at the C-terminus;
  (2) a factor B of a horseshoe crab; and
  (3) a proclotting enzyme of a horseshoe crab.

[2]

The measuring agent according to [1], wherein said factor B and said proclotting enzyme are derived from *Tachypleus tridentatus*.

[3]

The measuring agent according to [1] or [2], wherein said factor C is the protein (A) or (B) below; said factor B is the protein (C) or (D) below; and said proclotting enzyme is the protein (E) or (F) below:
  (A) a protein comprising the amino acid sequence shown in SEQ ID NO:2;
  (B) a protein comprising the amino acid sequence shown in SEQ ID NO:2 but which includes substitution, deletion, insertion, or addition of one or several amino acid residues, which protein has factor C activity;
  (C) a protein comprising the amino acid sequence shown in SEQ ID NO:4;
  (D) a protein comprising the amino acid sequence shown in SEQ ID NO:4 but which includes substitution, deletion, insertion, or addition of one or several amino acid residues, which protein has factor B activity;
  (E) a protein comprising the amino acid sequence shown in SEQ ID NO:6;
  (F) a protein comprising the amino acid sequence shown in SEQ ID NO:6 but which includes substitution, deletion, insertion, or addition of one or several amino acid residues, which protein has proclotting enzyme activity.

[4]

A method for producing the measuring agent according to any one of [1] to [3], the method comprising the steps (A) to (C) below:
  (A) a step of incorporating each of the DNAs (1) to (3) below into a viral DNA:
    (1) a DNA encoding a factor C derived from *Tachypleus tridentatus*, which factor C does not have His-tag sequence at the C-terminus;
    (2) a DNA encoding a factor B of a horseshoe crab; and
    (3) a DNA encoding a proclotting enzyme of a horseshoe crab;
  (B) a step of infecting insect cells with the virus into which said each DNA was incorporated; and
  (C) a step of allowing the insect cells infected with said each virus to express the protein encoded by said each DNA.

[5]

A method for producing the measuring agent according to any one of [1] to [3], the method comprising the steps (A) to (C) below:
  (A) a step of incorporating each of the DNAs (1) to (3) below into a vector:
    (1) a DNA encoding a factor C derived from *Tachypleus tridentatus*, which factor C does not have His-tag sequence at the C-terminus;
    (2) a DNA encoding a factor B of a horseshoe crab; and
    (3) a DNA encoding a proclotting enzyme of a horseshoe crab;
  (B) a step of introducing the vector, into which said each DNA was incorporated, into insect cells to incorporate said each DNA into the chromosome of the insect cells; and
  (C) a step of allowing the insect cells, into which said each DNA was incorporated, to express the protein encoded by said each DNA.

[6]

The method according to [4] or [5], wherein said DNA encoding factor C is the DNA (A) or (B) below; said DNA encoding factor B is the DNA (C) or (D) below; and said DNA encoding proclotting enzyme is the DNA (E) or (F) below:
  (A) a DNA comprising the nucleotide sequence shown in SEQ ID NO:1;
  (B) a DNA which hybridizes with the complementary sequence of the full length or a part of the nucleotide sequence shown in SEQ ID NO:1 under stringent conditions, and encodes a protein having factor C activity.
  (C) a DNA comprising the nucleotide sequence shown in SEQ ID NO:3 or 8;
  (D) a DNA which hybridizes with the complementary sequence of the full length or a part of the nucleotide sequence shown in SEQ ID NO:3 or 8 under stringent conditions, and encodes a protein having factor B activity.
  (E) a DNA comprising the nucleotide sequence shown in SEQ ID NO:5 or 9;
  (F) a DNA which hybridizes with the complementary sequence of the full length or a part of the nucleotide sequence shown in SEQ ID NO:5 or 9 under stringent conditions, and encodes a protein having proclotting enzyme activity.

[7]

A method for measuring endotoxin in a test sample, the method comprising a step of mixing the measuring agent according to any one of [1] to [3] with the test sample and a step of measuring progress of cascade reaction.

[8]

The method according to [7], which comprises a step of adding a substrate for detection of progress of cascade reaction to a reaction system.

[9]

The method according to [8], which further comprises a step of calculating the endotoxin level in the test sample on the basis of reaction of said substrate.

By the present invention, endotoxin can be rapidly and highly sensitively measured. For example, in one embodiment of the present invention, a detection sensitivity in the order of 0.0005 EU/mL can be achieved with only 30 minutes of measurement. Further, in the present invention, the expressed recombinant factor C, recombinant factor B, and recombinant proclotting enzyme can be used without purification, and hence, an endotoxin-measuring agent comprising these recombinant proteins can be simply and rapidly produced at a low cost.

BRIEF DESCRIPTION OF THE DRAWINGS

FIG. 1 is a diagram showing the cascade reaction system in a limulus test.

FIG. 2 is a diagram showing the structure of the vector pIZ/V5-His and the position of insertion of each of the genes. The arrow in the upper part indicates the position of insertion of the genes.

FIG. 3 is a photograph showing the expression levels of various factor Cs.

FIG. 4 is a diagram showing the activities of various factor Cs. In the Figure, "EU" denotes "endotoxin unit" which is a unit denoting the amount of endotoxin; "DW" denotes "distilled water; and "mAbs/min" represents the rate of increase in the absorbance (absorbance change rate).

FIG. 5 is a photograph showing the stability of the factor C expressed by the viral method.

FIG. 6 is a photograph showing the stability of the factor C expressed by the stably expressing cell method.

FIG. 7 is a diagram showing the effect of treatment by hollow fiber membrane filtration on the reactivities of the factors expressed by the viral method.

FIG. 8 is a diagram showing the reactivity of the endotoxin-measuring agent containing the factors expressed by the viral method. In the Figure, "Et" denotes "endotoxin".

FIG. 9 is a diagram showing the reactivity of the endotoxin-measuring agent containing the factors expressed by the stably expressing cell line method. (a) The reactivity at the endotoxin concentration of 0 to 0.1 EU/mL. (b) The reactivity at the endotoxin concentration of 0 to 0.01 EU/mL.

FIG. 10 is a photograph showing the purities and concentrations of the purified recombinant factor C and the purified naturally-occurring factor C. In the Figure, "rFC" denotes "recombinant Factor C"; "nFC" denotes naturally occurring Factor C.

FIG. 11 is a calibration curve showing a relationship between band intensities and amounts of BSA. The intensities of BSA bands on the gel stained with Coomassie brilliant blue as shown in FIG. 10 were quantified with a densitometer, and plotted against the concentrations of the BSA protein, to prepare the calibration curve.

FIG. 12 is a diagram showing the activities of the purified recombinant factor C and the purified naturally-occurring factor C.

DETAILED DESCRIPTION OF THE PREFERRED EMBODIMENT

In the present invention, a series of reactions wherein endotoxin activates factor C to produce active-type factor C; the active-type factor C activates factor B to produce active-type factor B; and the active-type factor B activates a proclotting enzyme to produce a clotting enzyme; may be referred to as "cascade reaction".

(1) Endotoxin-Measuring Agent of Present Invention

The endotoxin-measuring agent of the present invention comprises factor C, factor B, and a proclotting enzyme. The factor C, factor B, and proclotting enzyme comprised in the endotoxin-measuring agent of the present invention may be hereinafter referred to as "factor C of the present invention", "factor B of the present invention" and "proclotting enzyme of the present invention", respectively. Further, the factor C, factor B, and proclotting enzyme may be collectively referred to as "factors".

All of the factor C of the present invention, factor B of the present invention, and proclotting enzyme of the present invention are recombinant proteins obtainable by being expressed using insect cells as a host.

The factor C of the present invention is a factor C derived from a Japanese horseshoe crab *Tachypleus tridentatus*. The factor C of the present invention is characterized in that it does not have a His-tag attached at the C-terminus. Further, the factor C of the present invention preferably does not have a V5-tag at the C-terminus. Further, the factor C of the present invention more preferably does not have any peptide attached at the C-terminus. Further, the factor C of the present invention especially preferably does not have any peptide attached at either terminus. An amino acid sequence of the factor C of *Tachypleus tridentatus* is shown in SEQ ID NO:2. A nucleotide sequence of the gene encoding the factor C of *Tachypleus tridentatus* is shown in SEQ ID NO:1.

The factor C of the present invention may be a variant of the protein having the amino acid sequence shown in SEQ ID NO:2 as long as the variant has the factor C activity.

The "factor C activity" means an activity by which factor C becomes active-type factor C in the presence of endotoxin, to activate factor B. The fact that the factor C of the present invention "has the factor C activity" can be confirmed, for example, by using the factor C of the present invention in combination with a suitable factor B and a suitable proclotting enzyme, and detecting the progress of the cascade reaction in the presence of endotoxin. More particularly, the protein of SEQ ID NO:4 may be used as the suitable factor B, and the protein of SEQ ID NO:6 may be used as the suitable proclotting enzyme. The progress of the cascade reaction can be measured using the later-mentioned substrate for detection.

The factor C of the present invention may be a protein comprising the amino acid sequence shown in SEQ ID NO:2 but which includes substitution, deletion, insertion, or addition of one or several amino acid residues as long as the factor C has the factor C activity. The meaning of the term "one or several" varies depending on the positions of the amino acid residues in the three-dimensional structure of the protein and the types of the amino acid residues, and, more particularly, the term means preferably 1 to 20, more preferably 1 to 10, still more preferably 1 to 5, especially preferably 1 to 3. The above-described substitution, deletion, insertion, or addition of one or several amino acids is a conservative mutation that maintains the normal function of the protein. A representative example of the conservative mutation is a conservative substitution. The conservative substitution is, for example, a mutation wherein substitution takes place mutually among Phe, Trp, and Tyr, if the substitution site is an aromatic amino acid; among Leu, Ile, and Val, if the substitution site is a hydrophobic amino acid; between Gln and Asn, if the substitution site is a polar amino acid; among Lys, Arg, and His, if the substitution site is a basic amino acid; between Asp and Glu, if the substitution site is an acidic amino acid; and between Ser and Thr, if it the substitution site an amino acid having a hydroxyl group. Examples of substitutions considered as conservative substitutions include, specifically, substitution of Ser or Thr for Ala, substitution of Gln, His, or Lys for Arg, substitution of Glu, Gln, Lys, His, or Asp for Asn, substitution of Asn, Glu, or Gln for Asp, substitution of Ser or Ala for Cys, substitution of Asn, Glu, Lys, His, Asp, or Arg for Gln, substitution of Gly, Asn, Gln, Lys, or Asp for Glu, substitution of Pro for Gly, substitution of Asn, Lys, Gln, Arg, or Tyr for His, substitution of Leu, Met, Val, or Phe for Ile, substitution of Ile, Met, Val, or Phe for Leu, substitution of Asn, Glu, Gln, His, or Arg for Lys, substitution of Ile, Leu, Val, or Phe for Met, substitution of Trp, Tyr, Met, Ile, or Leu for Phe, substitution of Thr or Ala for Ser, substitution of Ser or Ala for Thr, substitution of Phe or Tyr for Trp, substitution of His, Phe, or Trp for Tyr, and substitution of Met, Ile, or Leu for Val. Further, the above-described substitution, deletion, insertion, addition, inversion or the like may also include a naturally occurring mutation due to difference in the individual, strain, or species among the horseshoe crabs from which the gene was derived.

Further, the factor C of the present invention may be a protein which has a homology or identity of not less than 80%, preferably not less than 90%, more preferably not less than 95%, still more preferably not less than 97%, especially preferably not less than 99% to the full length of the amino acid sequence of factor C as described above, for example, to the full length of the amino acid sequence shown in SEQ ID NO:2, and has the factor C activity.

The gene encoding the factor C of the present invention is not particularly restricted as long as the gene encodes the factor C of the present invention as described above. The gene encoding the factor C of the present invention may be a probe prepared based on a known gene sequence, for example, a DNA which hybridizes with the complementary sequence of the full length or a part of the nucleotide sequence shown in SEQ ID NO:1 under stringent conditions and encodes a protein having the factor C activity. The term "stringent conditions" herein means conditions under which the so-called specific hybrid is formed but a non-specific hybrid is not formed. Examples of the conditions include conditions under which highly homologous DNAs hybridize to each other, for example, DNAs not less than 80% homologous, preferably not less than 90% homologous, more preferably not less than 95% homologous, still more preferably not less than 97% homologous, especially preferably not less than 99% homologous, hybridize to each other, while DNAs less homologous than the above do not hybridize to each other; and conditions under which washing is carried out once, more preferably 2 or 3 times, at a salt concentration and temperature corresponding to 60° C., 1×SSC, and 0.1% SDS; preferably 60° C., 0.1×SSC, and 0.1% SDS; more preferably 68° C., 0.1×SSC, and 0.1% SDS; which are normal washing conditions in Southern hybridization.

Further, the combinations of the codons in the gene encoding the factor C of the present invention may be modified such that the gene is optimized for being expressed in insect cell. The optimization can be carried out using, for example, a generally available contract service. The gene encoding the factor C of the present invention may be a variant of a DNA whose combinations of the codons are optimized for expression in insect cells.

The above description on variants of the gene and protein may be applied similarly to the factor B and proclotting enzyme of the present invention, and to the genes encoding those.

The factor B of the present invention is a factor B derived from a horseshoe crab. Further, the proclotting enzyme of the present invention is a proclotting enzyme derived from a horseshoe crab. Examples of the horseshoe crab include a Japanese horseshoe crab *Tachypleus tridentatus*, American horseshoe crab *Limulus polyphemus*, Southeast Asian horseshoe crab *Carcinoscorpius rotundicauda* and Southeast Asian horseshoe crab *Tachypleus gigas*. The above factors are preferably derived from, among those horseshoe crabs, the Japanese horseshoe crab *Tachypleus tridentatus*.

Amino acid sequences of the factor B and proclotting enzyme of *Tachypleus tridentatus* are shown in SEQ ID NOs:4 and 6, respectively. Nucleotide sequences of the genes encoding the factor B and proclotting enzyme of *Tachypleus tridentatus* are shown in SEQ ID NOs:3 and 5, respectively.

The factor B of the present invention may be a variant of the factor B of any of the above-described horseshoe crabs, for example, a variant of the protein having the amino acid sequence shown in SEQ ID NO:4, as long as the factor B of the present invention has the factor B activity. Further, the gene encoding the factor B of the present invention is not particularly restricted as long as the gene encodes the factor B of the present invention as described above. The above description on factor C is also applied *mutatis mutandis* to the variants of the gene and protein.

The "factor B activity" means an activity by which factor B becomes active-type factor B in the presence of active-type factor C, to change a proclotting enzyme into its active form, a clotting enzyme. The fact that the factor B of the present invention "has the factor B activity" can be confirmed, for example, by using the factor B of the present invention in combination with a suitable factor C and a suitable proclotting enzyme, and detecting the progress of the cascade reaction in the presence of endotoxin. More particularly, the protein of SEQ ID NO:2 may be used as the suitable factor C, and the protein of SEQ ID NO:6 may be used as the suitable proclotting enzyme. The progress of the cascade reaction can be measured using the later-mentioned substrate for detection.

The proclotting enzyme of the present invention may be a variant of the proclotting enzyme of any of the above-described horseshoe crabs, for example, a variant of the protein having the amino acid sequence shown in SEQ ID NO:6, as long as the proclotting enzyme of the present invention has the proclotting enzyme activity. Further, the gene encoding the proclotting enzyme of the present invention is not particularly restricted as long as the gene encodes the proclotting enzyme of the present invention as described above. The above description on factor C is also applied *mutatis mutandis* to the variants of the gene and protein.

The "proclotting enzyme activity" means an activity by which a proclotting enzyme is changed to a clotting enzyme in the presence of active-type factor B, to react with the later-mentioned substrate for detection. The "activity to react with a substrate for detection" means, for example, an activity to react with coagulogen to cause coagulation, and an activity to react with Boc-Leu-Gly-Arg-pNA to release pNA. The fact that the proclotting enzyme of the present invention "has the proclotting enzyme activity" can be confirmed, for example, by using the clotting enzyme of the present invention in combination with a suitable factor C and a suitable factor B, and detecting the progress of the cascade reaction in the presence of endotoxin. More particularly, the protein of SEQ ID NO:2 may be used as the suitable factor C, and the protein of SEQ ID NO:4 may be used as the suitable factor B. The progress of the cascade reaction can be measured using the later-mentioned substrate for detection.

To the factor B of the present invention and/or the proclotting enzyme of the present invention, an arbitrary peptide or the like may be added as long as the factors have the factor B activity and the proclotting enzyme activity, respectively. Examples of such a peptide include tag sequences such as His-tag and V5-tag. Similarly to the factor C of the present invention, the factor B of the present invention and/or the proclotting enzyme of the present invention to be employed may be any of those wherein His-tag is not added to the C-terminus, those wherein V5-tag is not added to the C-terminus, those wherein no peptide is added to the C-terminus at all, and those wherein no peptide is added to either terminus at all.

Further, the combinations of the codons in the gene encoding the factor B of the present invention and/or the gene encoding the proclotting enzyme of the present invention may be modified such that the gene(s) is/are optimized for being expressed in insect cells. Examples of the DNA that encodes the factor B of SEQ ID NO:4 and has combinations of the codons optimized for expression in insect cells include the DNA of SEQ ID NO:8. Examples of the DNA that encodes the proclotting enzyme of SEQ ID NO:6 and has combinations of the codons optimized for expression in insect cells include the DNA of SEQ ID NO:9. Each of the gene encoding the factor B of the present invention and/or the gene encoding the proclotting enzyme of the present invention may be a variant of a DNA whose combinations of the codons are optimized for expression in insect cells.

The endotoxin-measuring agent of the present invention may consist of the factor C of the present invention, the factor B of the present invention, and the proclotting enzyme of the present invention.

The endotoxin-measuring agent of the present invention may comprise a substrate for detection of the progress of the cascade reaction. In the present invention, such a substrate may be referred to as "substrate for detection".

Examples of the substrate for detection include coagulogen. Due to contact of coagulogen with a clotting enzyme, coagulation occurs to produce coagulin. The progress of the coagulation reaction may be assayed by measuring the turbidity of the reaction solution. Coagulogen can be recovered from a horseshoe crab blood cell extract (lysate). Also, because a nucleotide sequence of the gene encoding coagulogen has been clarified (Miyata, et al., PROTEIN, NUCLEIC ACID AND ENZYME, Extra Edition, No. 29, pp. 30-43 (1986)), coagulogen can be produced according to a conventional method by genetic engineering.

As the substrate for detection, a synthetic substrate may also be used. The synthetic substrate is not particularly restricted as long as the substrate has a property suitable for detection, such as a property by which catalytic reaction of a clotting enzyme causes development of color or emission of fluorescence. Examples of the synthetic substrate include substrates represented by the general formula X-Y-Z (wherein X represents a protecting group, Y represents a peptide, and Z represents a dye bound to Y via an amide bond). In cases where endotoxin exists in the reaction system, catalytic reaction of a clotting enzyme, which is yielded as a result of the cascade reaction, cleaves the amide bond between Y and Z, to release the dye Z, leading to development of color or emission of fluorescence. The protecting group X is not particularly restricted, and a known protecting group for peptides may be suitably used. Examples of such a protecting group include the t-butoxycarbonyl group and the benzoyl group. The dye Z is not particularly restricted, and may be either a dye which can be detected under visible light or a fluorescent dye. Examples of the dye Z include pNA (para-nitroaniline), MCA (7-methoxycoumarin-4-acetic acid), DNP (2,4-dinitroaniline), and Dansyl dyes. Examples of the peptide Y include Leu-Gly-Arg (LGR), Ile-Glu-Gly-Arg (IEGR) (SEQ ID NO:12), and Val-Pro-Arg (VPR). The released dye Z may be measured by a method selected depending on the property of the dye.

Further, the endotoxin-measuring agent of the present invention may also comprise a component other than the factors and the substrate for detection, as long as the agent can be used for measurement of endotoxin. Such a component is not particularly restricted, and may be selected in consideration of preservability, ease of handling, and stability of the factors and the substrate for detection. The endotoxin-measuring agent of the present invention may comprise, for example, a pH-buffering agent and/or salt. Examples of the pH-buffering agent include HEPES buffer, MES buffer, Tris buffer, and GTA wide-range buffer. Organic solvents such as alcohols, esters, ketones, and amides may also be comprised in the endotoxin-measuring agent of the present invention.

The endotoxin-measuring agent of the present invention may be formulated into an arbitrary form including, for example, a solid form, liquid form, and gel form. For the formulation, additives normally used as formulation carriers such as vehicles; binders; disintegrants; lubricants; stabilizers; correctives; diluents; surfactants; and solvents may be used. The endotoxin-measuring agent of the present invention may be used for measuring endotoxin as it is, or after being diluted, dispersed, or dissolved in water, physiological saline, buffer, or the like. Needless to say, the resulting formulation obtained by such dilution, dispersion, or dissolution is also within the scope of the endotoxin-measuring agent of the present invention.

In the endotoxin-measuring agent of the present invention, the factors and the other components may exist as a mixture(s) or may separately exist. For example, the factors may be mixed at an arbitrary ratio to be formulated, or may be separately formulated.

The concentrations of the factors and the other components in the endotoxin-measuring agent of the present invention are not particularly restricted, and preferably adjusted such that the concentrations are within the later-mentioned preferred ranges when endotoxin is measured. The concentration of each of the factors in the endotoxin-measuring agent of the present invention (in terms of the solution prepared before contacting with the test sample) is, for example, preferably 20 to 100 μg/mL, more preferably 40 to 80 μg/mL, especially preferably about 60 μg/mL.

The endotoxin-measuring agent of the present invention may be provided as an endotoxin-measuring kit. The endotoxin-measuring kit is not particularly restricted as long as the kit contains the endotoxin-measuring agent of the present invention.

(2) Method for Producing Endotoxin-Measuring Agent of Present Invention

The factors to be comprised in the endotoxin-measuring agent of the present invention can be produced by being expressed using insect cells as a host.

The insect cells are not particularly restricted as long as the cells can express the factors, and cells normally used for expression of a heterologous protein may be suitably used. Examples of such insect cells include Sf9, Sf21, SF+, and High-Five. The insect cells are preferably Sf9.

The culture conditions under which the insect cells are cultured are not particularly restricted as long as the insect cells can be cultured under the conditions, and culture conditions normally used for culturing insect cells may be used after, if necessary, appropriately modified. For example, as a culture medium, one normally used for culturing insect cells may be used. Examples of such a medium include commercially available serum-free media for insect cells. More particularly, Sf900 II medium (Invitrogen) or the like may be suitably used. The cultivation may be carried out, for example, at 27° C. to 28° C. with shaking.

The method for expressing the factors using insect cells as a host is not particularly restricted as long as the factors can be expressed thereby, and a method normally used for expression of a heterologous protein can be suitably used. For example, each factor can be expressed by infecting insect cells with a virus into which a gene encoding the factor was incorporated (viral method). Alternatively, each factor can be expressed by introducing a vector, into which a gene encoding the factor was incorporated, into insect cells, thereby incorporating the gene into the chromosome of the host (stably expressing cell line method).

<Viral Method>

The virus to be used in the viral method is not particularly restricted as long as insect cells can be infected with the virus and the factors can be expressed thereby, and a virus normally used for expression of a protein in insect cells can be suitably used. Examples of such a virus include baculovirus. The baculovirus is preferably nucleopolyhedrovirus (NPV). Examples of the NPV include AcNPV (*Autographa californica* NPV) and BmNPV (*Bombix mori* NPV). The NPV is preferably AcNPV.

Introduction of the nucleic acid into the virus can be carried out by a conventional method, for example, by homologous recombination using a transfer vector. Examples of the transfer vector include pPSC8 (Protein Sciences), pFastBac (Invitrogen), and pVL1393 (Pharmingen). The transfer vector is preferably pPSC8.

By infecting, by a conventional method, insect cells with a virus into which the gene encoding each factor was incorporated, insect cells that harbor the virus and express the factor can be obtained.

<Stably Expressing Cell Line Method>

By incorporating the gene encoding each factor into the chromosome of insect cells, a stably expressing cell line, which stably expresses the factor, can be obtained. The method of construction of the stably expressing cell line is not particularly restricted, and the construction can be carried out by a conventional method. For example, the stably expressing cell line can be constructed using the pIZ/V5-His vector (Invitrogen) according to the manual.

In any case, the expressing cells are constructed such that the expressed factor C has the C-terminus to which Histag is not attached. Further, in cases where each factor is to be expressed without addition of any peptide, which is not restricted to His-tag at the C-terminus of the factor C, the expressing cells may be constructed such that no peptide is added.

In any case, the factors may be expressed together by a single type of expressing cells, or expressing cells may be constructed for each factor to express the respective factors separately.

Whether or not each factor is expressed can be confirmed by measuring the activity of the factor. Whether or not each factor is expressed can also be confirmed by measuring the amount of mRNA transcribed from the gene encoding the factor, or by detecting the factor by Western blotting using an antibody.

Each expressed factor may be recovered as a solution containing the factor, to be used as a component of the endotoxin-measuring agent of the present invention. The solution containing the factor may be, for example, a culture broth, culture supernatant, or cell extract, or a mixture thereof. Each factor may be used either after purification or without purification. In the present invention, an endotoxin-measuring agent having a sufficiently high performance can be provided even by using cell culture supernatant containing each expressed factor as it is without purification of the factor. In cases where each factor is to be purified, the purification may be carried out, for example, by a known method used for purification of a protein. Examples of such a method include ammonium sulfate precipitation, gel filtration chromatography, ion-exchange chromatography, hydrophobic interaction chromatography, and hydroxyapatite chromatography. In cases where a tag such as His-tag is attached to each factor, the factor may also be purified by affinity chromatography using affinity against the tag.

In cases where each factor was produced by the viral method, the virus is preferably eliminated. The method of elimination of the virus is not particularly restricted, and the elimination may be carried out by a conventional method. For example, the virus may be eliminated through a hollow-fiber filtration membrane having a pore size of 500 kDa.

(3) Method of Present Invention for Measuring Endotoxin

By mixing the endotoxin-measuring agent of the present invention with a test sample, the cascade reaction proceeds in cases where the test sample contains endotoxin. By measuring the progress of the cascade reaction, the endotoxin in the test sample can be measured. That is, the present invention provides a method for measuring endotoxin in a test sample, which method comprises a step of mixing the endotoxin-measuring agent of the present invention with a test sample, and a step of measuring the progress of the cascade reaction (hereinafter referred to as "first embodiment").

In the first embodiment, each factor comprised in the endotoxin-measuring agent of the present invention may have been contained in the reaction system from the beginning of the step of mixing the endotoxin-measuring agent of the present invention with a test sample, or may be sequentially added to the reaction system.

For example, the step of mixing the endotoxin-measuring agent of the present invention with a test sample may comprise the following steps (A) to (C):

(A) a step of adding the factor C of the present invention to the reaction system;

(B) a step of adding the factor B of the present invention to the reaction system; and (C) a step of adding the proclotting enzyme of the present invention to the reaction system.

Steps (A) to (C) may be carried out separately, partially at the same time, or totally at the same time. Steps (A) to (C) may be carried out in an arbitrary order. For example, Step (A) may be followed by Step (B), which may then be followed by Step (C).

In the first embodiment, the progress of the cascade reaction can be measured by adding a substrate for detection to the reaction system and then measuring the reaction of the substrate (coloring, coagulation, or the like). The substrate for detection may have been contained in the reaction system from the beginning of the step of mixing the endotoxin-measuring agent of the present invention with a test sample, or may be added to the reaction system during the progress or after completion of the step. The first embodiment, of course, includes cases where the endotoxin-measuring agent of the present invention which preliminarily contains a substrate for detection is employed.

As long as the cascade reaction proceeds in cases where endotoxin is contained in the test substance, the factor B and the proclotting enzyme of the present invention themselves may not necessarily contact with the test sample. That is, another embodiment of the method of the present invention for measuring endotoxin (hereinafter referred to as "second embodiment") is a method for measuring endotoxin in a test substance, which method comprises Steps (A) to (D) below.

(A) a step of mixing the factor C of the present invention with a test sample;

(B) a step of mixing the factor B of the present invention with the factor C after the mixing thereof in Step A;

(C) a step of mixing the proclotting enzyme of the present invention with the factor B after the mixing thereof in Step B; and (D) a step of measuring the progress of the cascade reaction.

In the second embodiment, Steps (A) to (D) may proceed separately, partially at the same time, or totally at the same time. For example, after beginning Step A, the factor B and/or proclotting enzyme may be added to the reaction system during the progress or after completion of the step. Alternatively, after beginning Step B, the proclotting enzyme may be added to the reaction system during the progress or after completion of the step. Alternatively, all the 3 factors may be contained in the reaction system from the beginning of Step A. Alternatively, for example, the factor C after the contacting in Step A may be recovered to be used in Step B, and the factor B after the contacting in Step B may be recovered to be used in Step C.

In the second embodiment, the progress of the cascade reaction may be measured by adding a substrate for detection to the reaction system and then measuring reaction of the substrate (coloring, coagulation, or the like). The substrate for detection may be contained in the reaction system from the beginning of Step A, or may be added to the reaction system during the progress or after completion of each step.

The method of the present invention for measuring endotoxin may comprise another arbitrary step as long as the cascade reaction proceeds in cases where the test sample contains endotoxin. For example, the method of the present invention for measuring endotoxin may comprise a step of adding a substrate for detection to the reaction system, or a step of mixing a clotting enzyme produced by the cascade reaction with a substrate for detection. Further, for example, the method of the present invention for measuring endotoxin may comprise a step of calculating the endotoxin level in the test sample on the basis of reaction of the substrate for detection.

In the method of the present invention for measuring endotoxin, the reaction is preferably carried out in an aqueous solvent such as water or a buffer.

In the method of the present invention for measuring endotoxin, the concentration of each factor in the reaction solution is not particularly restricted as long as the cascade reaction proceeds in cases where endotoxin is contained in the test sample, and may be set appropriately depending on the property of the factor and/or the like. For example, the concentration of each factor is usually 10 to 50 µg/mL, preferably 20 to 40 µg/mL, more preferably about 30 µg/mL, in terms of the final concentration.

In the method of the present invention for measuring endotoxin, the concentration of the substrate for detection in the reaction solution is not particularly restricted as long as the cascade reaction proceeds in cases where endotoxin is contained in the test sample, and may be set appropriately depending on the property of the substrate for detection and/or the like. For example, in cases where the substrate for detection is a synthetic substrate, the concentration of the substrate for detection is usually 0.001 mM to 100 mM, preferably 0.01 mM to 10 mM, in terms of the final concentration.

In any embodiment, the reaction system may contain an arbitrary component(s) other than the endotoxin-measuring agent in the first embodiment or the factors in the second embodiment, substrate for detection, and test sample, as long as the cascade reaction proceeds in cases where endotoxin is contained in the test sample. For example, the reaction system may contain a pH-buffering agent and/or salt. Examples of the pH-buffering agent include HEPES buffer, MES buffer, Tris buffer, and GTA wide-range buffer. Organic solvents such as alcohols, esters, ketones, and amides may also be contained in the reaction system.

The pH of the reaction solution is not particularly restricted as long as the cascade reaction proceeds in cases where endotoxin is contained in the test sample, and may be set appropriately depending on the property of each factor. For example, the pH of the reaction solution is usually 5 to 10, preferably 7 to 8.5.

The reaction temperature is not particularly restricted as long as the cascade reaction proceeds in cases where endotoxin is contained in the test sample, and may be set appropriately depending on the property of each factor. The reaction temperature is, for example, usually 10° C. to 80° C., preferably 20° C. to 50° C. For example, the reaction temperature may be room temperature.

The reaction time is not particularly restricted, and may be set appropriately depending on conditions such as the property of each factor and the reaction temperature. The reaction time is, for example, usually 5 minutes to 1 hour, preferably 15 minutes to 45 minutes. For example, the reaction time may be 30 minutes.

In any embodiment, during the process of reaction, the test sample, factors, and other components may be additionally added, individually or in an arbitrary combination, to the reaction system. These components may be added at once or in a plurality of times, or may be added continuously. Constant conditions may be employed from the beginning of the reaction to the end of the reaction, or conditions may be changed during the process of reaction.

By measuring reaction of the substrate for detection (coloring, coagulation, or the like), the progress of the cascade reaction due to existence of endotoxin can be measured, and hence the endotoxin in the test substance can be measured. The reaction of the substrate for detection (coloring, coagulation, or the like) may be measured by a method depending on the substrate for detection employed.

In cases where the measurement of endotoxin is carried out quantitatively, an endotoxin standard sample whose concentration is known may be used to obtain a correlation data between the endotoxin level and the degree of reaction of the substrate for detection (degree of coloring, coagulation, or the like), and, endotoxin existing in the test sample may be quantified on the basis of the correlation data. The correlation data may be, for example, a calibration curve. The quantification may be carried out either by the kinetic method or by the end point method.

The test sample to be subjected to the measurement of endotoxin is not particularly restricted, and examples thereof include medical water, pharmaceuticals, infusion solutions, blood preparations, medical equipments, medical apparatuses, cosmetics, foods and beverages, environmental samples (e.g., airs, rivers, and soils), biological components (e.g., bloods, body fluids, and tissues), naturally occurring proteins, recombinant proteins, nucleic acids, and carbohydrates. The test sample may be subjected to the measurement of endotoxin by mixing, dispersing, or dissolving the test sample as it is or an extract or washing solution of the test sample in a reaction system.

EXAMPLES

The present invention will now be described by way of Examples more particularly. However, these are merely examples of the present invention, and the scope of the present invention is not limited to these.

Example 1: Production of Endotoxin-Measuring Agent of Present Invention (1-1) Method Using Virus (Hereinafter Referred to as "Viral Method")

In the present Example, a recombinant baculovirus into which the gene encoding each of factor C, factor B, and a proclotting enzyme was incorporated was used to express the factor in insect cells, and an endotoxin-measuring agent was thereby produced.

(1-1-1) Preparation of Recombinant Baculovirus

As a DNA encoding His-tag-attached factor C (His-tag-attached factor C gene), the DNA of SEQ ID NO:7 was totally synthesized using a generally available contract service (TAKARA BIO INC.). The His-tag-attached factor C is the factor C of a Japanese horseshoe crab shown in SEQ ID NO:2 wherein a 6×His-tag is attached to the C-terminus. The DNA was inserted between the recognition sites of restriction enzymes NruI and SmaI of a transfer vector pPSC8 (Protein Sciences), to obtain a vector for recombination. Using the vector for recombination, the His-tag-attached factor C gene was incorporated into a baculovirus AcNPV, to prepare a recombinant baculovirus.

Further, using a primer FC-N-Pst (SEQ ID NO:10) and a primer FC-notag-R-Bam (SEQ ID NO:11), and the above-described DNA encoding the His-tag-attached factor C as a template, PCR was carried out to prepare a DNA encoding factor C wherein the nucleotide sequence encoding the His-tag sequence at the 3'-end was removed (His-tag-free factor C gene). The DNA encodes the Japanese horseshoe crab factor C shown in SEQ ID NO:2, wherein no His tag is attached at the C-terminus. Also for the His-tag-free factor C gene, a recombinant baculovirus was prepared by the same method as described above.

As a DNA encoding factor B (factor B gene), the DNA of SEQ ID NO:8 was totally synthesized using a generally available contract service (TAKARA BIO INC.). The DNA encodes the Japanese horseshoe crab factor B shown in SEQ ID NO:4 (His-tag free), and the combinations of its codons are optimized for expression in insect cells. Also for the factor B gene, a recombinant baculovirus was prepared by the same method as described above. However, the position of insertion in the pPSC8 vector was between the recognition sites of restriction enzymes PstI and KpnI.

As a DNA encoding the proclotting enzyme (proclotting enzyme gene), the DNA of SEQ ID NO:9 was totally synthesized using a generally available contract service (TAKARA BIO INC.). The DNA encodes the Japanese horseshoe crab proclotting enzyme shown in SEQ ID NO:6 (His-tag free), and the combinations of its codons are optimized for expression in insect cells. Also for the proclotting enzyme gene, a recombinant baculovirus was prepared by the same method as described above. However, the position of insertion in the pPSC8 vector was between the recognition sites of restriction enzymes XbaI and BglII.

(1-1-2) Infection of Insect Cells (Sf9 Cells) with Recombinant Baculovirus

Sf9 cells (Novagen) were inoculated in a medium at $1.5 \times 10^6$ cells/mL, and the recombinant baculovirus, into which the DNA encoding the His-tag-attached factor C was introduced, was added to the medium, to infect the cells with the virus. As the medium for the Sf9 cells, Sf900 II medium (Invitrogen) supplemented with antibiotics (antibiotics-antifungal agents (×100); Invitrogen) (final concentration, ×1) (1 L) was used. The multiplicity of infection (MOI) of the virus was set to 1.0. Thereafter, the obtained cells were cultured at 28° C. for 48 hours with shaking.

Similarly, Sf9 cells were infected with the virus into which the DNA encoding the His-tag-free factor C was introduced.

Further, Sf9 cells were infected also with each of the virus to which the DNA encoding the factor B was introduced and the virus to which the DNA encoding the proclotting enzyme was introduced. In these cases, MOI was set to 0.5, and the culturing time was 72 hours.

(1-1-3) Recovery of Solution of Expressed Recombinant Protein

Each of the culture broths obtained after the above culturing was centrifuged at 4° C. at 3000×g for 30 minutes to obtain the supernatant, which was then stored at −80° C.

(1-1-4) Removal of Impurities and Viruses from Recombinant Protein Solution

Each of the supernatants which had been stored frozen as described above was thawed, and applied to a filter having a pore size of 0.1 µm (Cup Filter (Millipore)). Filtration was carried out with suction, and the solution which had passed through the filter was recovered. Each recovered supernatant was applied to a hollow fiber filtration membrane having a pore size of 500 kDa (polyether sulfone hollow fiber membrane; Spectrum Labs) and filtered using the Kros Flow TFF pump filtration system (Spectrum Labs). Each solution which had passed through the membrane was recovered.

(1-1-5) Preparation of Reagent

At 4° C., 560 mL of each solution obtained in the above (1-1-4) (wherein factor C, factor B, or proclotting enzyme is contained), 134 mL of distilled water, 126 mL of 6.66 mM aqueous solution of a synthetic substrate (Boc-Leu-Gly-Arg-pNA) (final concentration, 0.3 mM) and 560 mL of 15% aqueous dextran solution (final concentration, 3%) were mixed together. This mixture was aliquoted in 5 mL-volumes into vials and freeze-dried, to provide the endotoxin-measuring agent 1.

(1-2) Method Using Plasmid (Hereinafter Also Referred to as "Stably Expressing Cell Line Method")

In the present Example, a gene encoding each of the factor C, factor B, and proclotting enzyme was incorporated into the chromosome of insect cells to construct a stably expressing cell line, and each factor was then expressed, thereby producing an endotoxin-measuring agent.

(1-2-1) Preparation and Cultivation of Stably Expressing Cell Line

Each of the His-tag-free factor C gene, factor B gene (SEQ ID NO:8), and proclotting enzyme gene (SEQ ID NO:9) used in the above-described viral method was introduced into Sf9 cells (Invitrogen) using the pIZ vector kit (Invitrogen).

More particularly, each of the DNAs was firstly incorporated between the EcoRV and MluI recognition sites in a vector pIZ/V5-His comprised in the kit, and the resulting each vector was mixed with Cellfectin comprised in the kit, followed by introduction of the vector into Sf9 cells. The position of incorporation of the DNAs in pIZ/V5-His, and the like are shown in FIG. 2. In the region indicated by a thick arrow shown at the top in FIG. 2, each one of the DNAs was incorporated. As the medium for the Sf9 cells, Sf900 III medium (Invitrogen) supplemented with antibiotics (antibiotics-antifungal agents (×100); Invitrogen) (final concentration, ×1) and Zeocin antibiotic (Invitrogen) (final concentration, 50 µg/mL) was used. The density of the thus obtained cell line, into which each DNA was introduced, was adjusted to $6 \times 10^5$ cells/mL (1 L) in the medium, and the cells were cultured at 28° C. for 96 hours with shaking.

It should be noted that, although a His tag sequence is contained in pIZ/V5-His, all of the above described DNAs have a stop codon, so that all of the factor C, factor B, and proclotting enzyme are expressed without addition of His-tag.

(1-2-2) Recovery of Solution of Recombinant Protein, Removal of Impurities, and Preparation of Reagent Each culture broth obtained after the above-described culturing was processed in the same manner as described in "(1-1-3) Recovery of Solution of Expressed Recombinant Protein", "(1-1-4) Removal of Impurities and Viruses from Recombinant Protein Solution" and "(1-1-5) Preparation of Reagent" for the viral method. However, the process of filtration using a hollow fiber filtration membrane in "(1-1-4) Removal of Impurities and Viruses from Recombinant Protein Solution" was not carried out. The thus obtained measuring agent was provided as the endotoxin-measuring agent 2.

Example 2: Properties and the Like of Expressed Proteins (2-1) Comparison of Expression Level of Factor C The expression level was compared among the His-tag-free factor Cs obtained by the viral method and the stably expressing cell line method, and the His-tag-attached factor C obtained by the viral method.

The expression level was evaluated by sampling 0.5, 1.5, 5, or 15 μL of the solution corresponding to the one after the filtration and before the preparation of the reagent in Example 1 and subjecting the sampled solutions to 5-20% polyacrylamide gel electrophoresis (under non-reducing conditions) in the presence of SDS and then to Western blotting using an anti-factor C antibody (2C12, obtained from Prof. Shun-ichiro Kawabata, Department of Biology, Graduate School of Sciences, Kyushu University).

The results are shown in FIG. 3. The results indicate that the expression levels of the His-tag-free factor Cs were lower than the expression level of the His-tag-attached factor C. Further, the intensities of the bands on the Western blot in FIG. 3 were measured using a densitometer, and, the volume ratio of each solution with which equal concentrations of the factor Cs are attained was calculated on the basis of relative values of the measured intensities. The volume ratio was 50 as for the His-tag free factor C obtained by the viral method, 17 as for the His-tag free factor C obtained by the stably expressing cell line method, and 7 as for the His-tag-attached factor C obtained by the viral method.

(2-2) Comparison of Activity of Factor C

The proclotting enzyme-activating capacity of each of the factor C solutions was studied using an equal amount of factor C.

More particularly, each of the His-tag-attached factor C solution obtained by the viral method (0.7 μL or 5 μL), His-tag-free factor C solution obtained by the viral method (5 μL), and His-tag-free factor C solution obtained by the stably expressing cell line method (1.7 μL) was placed in a well of a 96-well plate. Thereafter, the factor B-containing solution (5 μL) and the proclotting enzyme-containing solution (5 μL) obtained after the filtration through the 0.1 μm filter in (1-1-4) in the viral method in Example 1, and Boc-Leu-Gly-Arg-pNA (final concentration, 0.3 mM), Tris-HCl (pH 8.0) (final concentration, 100 mM), and 50 μL of endotoxin (product name "USP-Reference Standard Endotoxin" (USP-RSE); commercially available from Seikagaku Biobusiness Corporation) (sample concentration: 0, 0.05, or 0.5 EU/mL) were added to each well such that the total volume in the well became 100 μL, and mixed together, followed by incubation at 37° C. for 3 hours, during which the absorbance at 405 nm was measured with time. As a negative control, distilled water was used. The rate of increase in the absorbance (the absorbance change rate) reflects the proclotting enzyme-activating capacity. The term "EU" means the "endotoxin unit", which is a unit representing the amount of endotoxin (this also applies hereinafter).

The results are shown in FIG. 4. In FIG. 4, "DW" means distilled water; "Virus+His tag (×1)" means the His-tag-attached factor C solution obtained by the viral method (0.7 μL); "Virus+His tag (×7)" means the same solution (5 μL); "Virus No tag (×1)" means the His-tag free factor C solution obtained by the viral method; and "Stable Sf9 No tag (×1)" means the His-tag free factor C solution obtained by the stably expressing cell line method.

As a result, activation of the proclotting enzyme was not observed or hardly observed in the His-tag-attached factor C solution containing the equal amount of factor C (0.7 μL), and even in the solution containing about 7 times the amount of factor C (5 μL). On the other hand, the His-tag-free factor C showed a remarkable proclotting enzyme-activating capacity irrespective of whether it was obtained by the viral method or by the stably expressing cell line method.

From the above results, it was shown that a recombinant factor C molecule expressed without addition of His-tag sequence has a much stronger proclotting enzyme-activating capacity than a recombinant factor C molecule expressed with addition of His-tag sequence. Further, it was shown that each of the expressed proteins can be used without purification, in the state where the protein is contained in the culture supernatant.

(2-3) Comparison of Stability of Expressed Factor C (2-3-1) Stability of Factor C Expressed by Viral Method In the step of culturing the virus-infected cells at 28° C. with shaking in (1-1-2) in the viral method in Example 1, the supernatant was recovered after 48 hours, 72 hours, and 96 hours of cultivation, and each recovered supernatant was subjected to 5-20% polyacrylamide gel electrophoresis (under non-reducing conditions) in the presence of SDS, followed by evaluation of the remaining amount of the factor C by Western blotting using the anti-factor C antibody (2C12, which is the same as the one used above). Further, sampling and analysis were separately carried out in the same manner for the supernatant obtained by adding a protease inhibitor (leupeptin at a final concentration of 0.5 μg/mL+pepstatin A at a final concentration of 0.7 μg/mL) to the culture broth after 24 hours of the infection with the virus.

The results are shown in FIG. 5. As a result, it was shown that the factor C expressed by the viral method was decomposed with time during the cultivation. Further, it was shown that decomposition of the factor C also occurred to some extent in the case where the protease inhibitor was added.

(2-3-2) Stability of Factor C Expressed by Stably Expressing Cell Line Method

Similarly, in the step of culturing the stably expressing cell line at 28° C. with shaking in (1-2-1) in the stably expressing cell line method in Example 1, the supernatant was recovered after 72 hours, 96 hours, 120 hours, 144 hours, and 168 hours of cultivation, and each recovered supernatant was subjected to 5-20% polyacrylamide gel electrophoresis (under non-reducing conditions) in the presence of SDS, followed by evaluation of the remaining amount of the factor C by Western blotting using the anti-factor C antibody (2C12, which is the same as the one used above). Further, the supernatant obtained after 48 hours of cultivation by the viral method was also applied.

The results are shown in FIG. 6. As a result, the factor C expressed by the stably expressing cell line method has not been decomposed in the absence of a protease inhibitor even after 168 hours of cultivation. By this, it was shown that use of the stable expressing cell line method can prevent decomposition of factor C.

(2-4) Study on Whether Treatment by Hollow Fiber Membrane Filtration Is Necessary Whether the treatment by a hollow fiber filtration membrane in (1-1-4) in the viral method is necessary was studied. Using each solution sampled before filtration through the hollow fiber membrane in (1-1-4) and each solution sampled after filtration therethrough (3 lots) in (1-1-4), the rate of increase in the absorbance (the absorbance change rate) was measured in the same manner as in the above (2-2), by adding endotoxin (USP-RSE) to a final concentration of 0 or 0.05 EU/mL.

The results are shown in FIG. 7. In FIG. 7, "unfiltered solution" means a solution remained in the hollow fiber membrane cartridge without being filtered. In the cases where each solution sampled after filtration through the hollow fiber membrane was used, the degree of activation of the proclotting enzyme was low when the concentration of endotoxin was 0 EU/mL (in other words, the blank value upon endotoxin measurement was low), and that is, an excellent result was obtained. By contorast, it was revealed that, in the cases where each solution sampled before filtration through the hollow fiber membrane ("before filtration" or "unfiltered solution") was used, the degree of activation of the proclotting enzyme was high even in the cases of 0 EU/mL of endotoxin, which leads to a high blank value upon endotoxin measurement.

By contrast, by the stably expressing cell line method, the degree of activation of the proclotting enzyme in the case of 0 EU/mL of endotoxin (the blank value upon endotoxin measurement) was kept low even without such a process of filtration through the hollow fiber filtration membrane (FIG. 4).

From these results, it was shown that, while filtration through a hollow fiber filtration membrane is indispensable in cases where the viral method is used, such filtration is not necessary in cases where the stably expressing cell line method is used.

Example 3: Measurement of Endotoxin Using Endotoxin-Measuring Agent of Present Invention (3-1) Measurement Using Endotoxin-Measuring Agent 1

To the endotoxin-measuring agent 1 (freeze-dried product), 3.3 mL of 100 mM Tris buffer (pH 8.0) was added, to dissolve the agent. In this solution, the protein concentration of each of the culture supernatants containing the factor C, factor B, and proclotting enzyme was about 60 μg/mL.

Into each well of a 96-well microtiter plate, 50 μL of an endotoxin solution at a concentration of 0, 0.001, 0.01, or 0.1 EU/mL was aliquoted, and 50 μL of the endotoxin-measuring agent solution prepared by dissolving the agent was added to the each well, followed by mixing the resulting mixture. The mixture was then incubated at 37° C. for 30 minutes, and the endotoxin concentration was measured according to the reaction rate method in which the absorbance at 405 nm was measured with time during the incubation. In this reaction solution, the protein concentration of each of the culture supernatants containing the factor C, factor B, and proclotting enzyme was about 30 μg/mL.

The results are shown in FIG. 8. As a result, it was shown that, in cases where the factors expressed by the viral method are used, the absorbance change rate linearly increases within the range of 0.001 to 0.10 EU/mL as the concentration of endotoxin increases.

(3-2) Measurement Using Endotoxin-Measuring Agent 2

To the endotoxin-measuring agent 2 (freeze-dried product), 3.3 mL of 100 mM Hepes buffer (pH 7.6) was added, to dissolve the agent. In this solution, the protein concentration of each of the culture supernatants containing the factor C, factor B, and proclotting enzyme was about 60 μg/mL.

Into each well of a 96-well microtiter plate, 50 μL of an endotoxin solution at a concentration of 0, 0.0005, 0.001, 0.005, 0.01, or 0.1 EU/mL was aliquoted, and 50 μL of the endotoxin-measuring agent solution prepared by dissolving the agent was added to the each well, followed by mixing the resulting mixture. The mixture was then incubated at 37° C. for 30 minutes, and the endotoxin concentration was measured according to the reaction rate method in which the absorbance at 405 nm was measured with time during the incubation. In this reaction solution, the protein concentration of each of the culture supernatants containing the factor C, factor B, and proclotting enzyme was about 30 μg/mL.

The results are shown in FIG. 9. As a result, it was shown that, in cases where the factors expressed by the stably expressing cell method are used, the absorbance change rate linearly increases within the range of 0.0005 to 0.1 EU/mL as the concentration of endotoxin increases.

Based on the above results, with either of the endotoxin-measuring agents, quantification of endotoxin at a concentration of 0.001 EU/mL was possible within 30 minutes. Further, with the endotoxin-measuring agent 2, endotoxin at a concentration of 0.0005 EU/mL was able to be measured within 30 minutes. Thus, it was shown that the endotoxin-measuring agents of the present invention enable more rapid and sensitive quantification of endotoxin compared to the conventional methods (by which the measurement takes not less than 1 hour, and the detection sensitivity of 0.001 EU/mL has not been achieved). Further, it was shown that, in either case, the expressed factors can be used for a measuring agent as they are without purification.

Example 4: Difference in Activity Between Recombinant Factor C Protein and Naturally Occurring Factor C Protein (4-1) Purification of Recombinant Factor C Protein and Naturally Occurring Factor C Protein By covalently bonding 2 mg of the anti-factor C antibody (2C12, which is the same as the one used above) to sepharose column 1 ml (GE Healthcare), 2 factor-C antibody columns were prepared. The preparation was carried out according to the method described in the attached instructions. To 76 mL of culture supernatant containing recombinant factor C protein derived by the stably expressing cell method that was prepared by the same process as described in the above "(1-2-2) Recovery of Recombinant Protein", an equal amount of 20 mM Tris-HCl buffer (pH 8.0) containing 2 M sodium chloride and 2 mM EDTA was added to dilute the culture supernatant, followed by subjecting the resulting dilution to one of the factor-C antibody columns. Similarly, to 76 mL of an extract of horseshoe crab blood cells, an equal amount of 20 mM Tris-HCl buffer (pH 8.0) containing 2 M sodium chloride and 2 mM EDTA was added to dilute the extract, followed by subjecting the resulting dilution to the other of the factor-C antibody columns. The both columns were washed sequentially with 20 mL each of 20 mM Tris-HCl buffer (pH 8.0) containing 200 mM or 450 mM sodium chloride, and elution was then carried out with 50 mM glycine buffer (pH 2.5). Into a 1.5 mL tube in which 0.025 mL of 1M Trizma base (Sigma) was preliminarily placed, 1 mL of each eluted fraction was collected, to return the pH of the eluted solution to neutral.

(4-2) Comparison of Concentration between Purified Recombinant and Naturally Occurring Factor C Proteins The eluted fractions of the purified recombinant and naturally occurring factor C proteins were subjected to separation by 5-20% polyacrylamide gel electrophoresis (under non-reducing conditions) in the presence of SDS. In this process, purified bovine serum albumin (=BSA) whose concentration is known was also subjected to separation on the same gel as samples for concentration reference (FIG. 10). The intensities of BSA bands on the gel stained with Coomassie brilliant blue were quantified with a densitometer, and plotted against the concentrations of the BSA protein, to prepare a calibration curve (FIG. 11). Based on the band intensities of the purified factor C proteins and the calibration curve, the concentrations of the purified factor C proteins were approximated. As a result, it was revealed that, as for the purified samples, the naturally occurring factor C protein had about 4 times the concentration of the recombinant factor C protein.

(4-3) Comparison of Activity Between Purified Recombinant and Naturally Occurring Factor C Proteins A comparison of the activity was made using the purified recombinant and naturally occurring factor C proteins. In this comparison, the protein concentration was equalized between the purified factor Cs based on the results of (4-2). Into each well of a 96-well microtiter plate, 50 μL of an endotoxin solution at a concentration of 0, 0.05, 0.1, or 0.5 EU/mL was aliquoted. Reagents and culture supernatants were added to the each well such that 50 mM Tris buffer (pH 8.0), 0.2 μg/mL purified factor C protein, μg/mL protein of each of culture supernatants containing the recombinant factor B and recombinant proclotting enzyme, and 0.3 mM of the synthetic substrate Boc-Leu-Gly-Arg-pNA were contained in the reaction solution, whose total volume was adjusted to 100 μL by addition of water for injection. The reaction solution was incubated at 37° C. for 30 minutes, and the analysis was carried out according to the reaction rate method in which the absorbance at 405 nm was measured with time during the incubation.

As a result, it was revealed that the purified recombinant factor C protein had about twice the activity of the purified naturally occurring factor C protein (FIG. 12). The above results suggest that the recombinant factor C has a higher specific activity than the naturally occurring factor C.

INDUSTRIAL APPLICABILITY

By the present invention, endotoxin can be rapidly and highly sensitively measured. Further, by the present invention, an endotoxin-measuring agent can be simply and rapidly produced at a low cost. Therefore, the present invention can be extremely effectively used for detection of endotoxin.

DESCRIPTION OF SEQUENCE LISTING

SEQ ID NO:1 DNA sequence of factor C gene of Japanese horseshoe crab
SEQ ID NO:2 Amino acid sequence of factor C of Japanese horseshoe crab
SEQ ID NO:3 DNA sequence of factor B gene of Japanese horseshoe crab
SEQ ID NO:4 Amino acid sequence of factor B of Japanese horseshoe crab
SEQ ID NO:5 DNA sequence of proclotting enzyme gene of Japanese horseshoe crab
SEQ ID NO:6 Amino acid sequence of proclotting enzyme of Japanese horseshoe crab
SEQ ID NO:7 DNA sequence of His-tag-attached factor C gene
SEQ ID NO:8 DNA sequence of factor B gene whose codons are optimized for expression in insect cells
SEQ ID NO:9 DNA sequence of proclotting enzyme gene whose codons are optimized for expression in insect cells
SEQ ID NO:10 Primer for preparation of His-tag-free factor C gene
SEQ ID NO:11 Primer for preparation of His-tag-free factor C gene
SEQ ID NO:12 Peptide sequence

What is claimed is:

1. A method for producing an endotoxin measuring agent, comprising:
   (a) incorporating each of DNAs (1) to (3) below into three vectors respectively, with the proviso that the vector is not a virus:
      (1) a DNA encoding a factor C, which DNA is DNA (A') or (B') below, and which factor C does not have His-tag sequence or any peptide attached at the C terminus:
         (A') a DNA having a sequence consisting of the nucleotide sequence shown in SEQ ID NO:1;
         (B') a DNA encoding a protein having a sequence consisting of an amino acid sequence having an identity of 90% or higher to the amino acid sequence shown in SEQ ID NO:2, wherein the protein has factor C activity greater than the activity of natural factor C under the same condition;
      (2) a DNA encoding a factor B of a horseshoe crab; and
      (3) a DNA encoding a proclotting enzyme of a horseshoe crab;
   (b) introducing the three vectors, into which said each DNA was incorporated, into insect cells to incorporate said each DNA into a chromosome of the insect cells;
   (c) allowing the insect cells, into which said each DNA was incorporated, to express the protein encoded by said each DNA;
   (d) recovering a solution comprising the expressed proteins; and
   (e) formulating the endotoxin measuring agent comprising the expressed proteins.

2. A method for producing a factor C recombinant protein for use in an endotoxin measuring agent, comprising:
   (a) incorporating a DNA encoding the factor C recombinant protein into a vector, wherein the factor C recombinant protein encoded by the DNA is a protein (A) or (B) below, and does not have His-tag sequence or any peptide attached at the C-terminus, with the proviso that the vector is not a virus:
      (A) a protein consisting of an amino acid sequence shown in SEQ ID NO:2;
      (B) a protein consisting of an amino acid sequence having an identity of 90% or higher to the amino acid sequence shown in SEQ ID NO:2, wherein the protein has factor C activity greater than the activity of natural factor C under the same condition;
   (b) introducing the vector, into which said DNA was incorporated, into insect cells to incorporate said DNA into a chromosome of the insect cells;
   (c) allowing the insect cells, into which said DNA was incorporated, to express the factor C recombinant protein encoded by said DNA; and
   (d) recovering a solution containing the expressed protein.

3. The method according to claim 2, wherein said factor C recombinant protein does not have any peptide attached at the C-terminus.

4. The method according to claim 2, wherein said insect cell is at least one selected from the group consisting of Sf9, Sf21, SF+, and High-Five.

5. The method according to claim 1, wherein said vector is a plasmid.

6. The method according to claim 2, wherein said vector is a plasmid.

7. The method according to claim 2, wherein said factor C recombinant protein does not have V5 tag attached at the C-terminus.

8. The method according to claim 1, wherein said factor C does not have V5 tag attached at the C-terminus.

9. The method according to claim 1, wherein said factor C does not have any peptide at the C-terminus.

10. The method according to claim 1, wherein said insect cell is at least one selected from the group consisting of Sf9, Sf21, SF+, and High-Five.

* * * * *

UNITED STATES PATENT AND TRADEMARK OFFICE
CERTIFICATE OF CORRECTION

PATENT NO. : 11,162,949 B2
APPLICATION NO. : 15/984288
DATED : November 2, 2021
INVENTOR(S) : Hikaru Mizumura et al.

It is certified that error appears in the above-identified patent and that said Letters Patent is hereby corrected as shown below:

On the Title Page

Column 2, Line 4, item (56), under Other Publications, delete "Invitrogen_ plZV5vector_kit," and insert --Invitrogen_plZV5vector_kit,--.

Column 2, Line 9, item (56), under Other Publications, delete "ews" and insert --news--.

Column 2, Line 12, item (56), under Other Publications, delete "rotandicauuda)," and insert --rotundicauda),--.

Column 2, Line 14, item (56), under Other Publications, delete "lle-lle" and insert --Ile-Ile--.

In the Specification

In Column 4, Line 20, delete "activity." and insert --activity;--.

In Column 4, Line 26, delete "activity." and insert --activity;--.

In Column 11, Line 9, delete "(Bombix" and insert --(Bombyx--.

In Column 11, Line 31, delete "Histag" and insert --His-tag--.

In Column 15, Line 19, delete "Nrul" and insert --NruI--.

In Column 15, Line 19, delete "Smal" and insert --SmaI--.

In Column 19, Line 26, delete "contorast," and insert --contrast,--.

In Column 21, Line 35, after "protein," insert --30--.

Signed and Sealed this
Twenty-fifth Day of January, 2022

Drew Hirshfeld
*Performing the Functions and Duties of the*
*Under Secretary of Commerce for Intellectual Property and*
*Director of the United States Patent and Trademark Office*